(12) United States Patent
Lee et al.

(10) Patent No.: US 10,196,627 B2
(45) Date of Patent: Feb. 5, 2019

(54) CARBON FIXATION CYCLE AND USE THEREOF

(71) Applicant: Sogang University Research Foundation, Seoul (KR)

(72) Inventors: Jeong Kug Lee, Seoul (KR); Eui Jin Kim, Seoul (KR); Kyu Ho Lee, Seoul (KR)

(73) Assignee: Sogang University Research Foundation, Seoul (KR)

( * ) Notice: Subject to any disclaimer, the term of this patent is extended or adjusted under 35 U.S.C. 154(b) by 0 days.

(21) Appl. No.: 15/121,048

(22) PCT Filed: Feb. 24, 2015

(86) PCT No.: PCT/KR2015/001743
§ 371 (c)(1),
(2) Date: Nov. 8, 2016

(87) PCT Pub. No.: WO2015/126221
PCT Pub. Date: Aug. 27, 2015

(65) Prior Publication Data
US 2017/0166880 A1    Jun. 15, 2017

(30) Foreign Application Priority Data
Feb. 24, 2014 (KR) ........................ 10-2014-0021442

(51) Int. Cl.
*C12N 9/00* (2006.01)
*C12N 9/02* (2006.01)
*C12N 9/04* (2006.01)
*C12N 9/88* (2006.01)
*C12P 7/40* (2006.01)

(52) U.S. Cl.
CPC ............. *C12N 9/93* (2013.01); *C12N 9/0006* (2013.01); *C12N 9/0008* (2013.01); *C12N 9/88* (2013.01); *C12P 7/40* (2013.01); *C12Y 101/01041* (2013.01); *C12Y 101/01042* (2013.01); *C12Y 102/07003* (2013.01); *C12Y 401/03001* (2013.01); *C12Y 602/01004* (2013.01)

(58) Field of Classification Search
None
See application file for complete search history.

(56) References Cited

U.S. PATENT DOCUMENTS

2011/0008861 A1    1/2011 Berry et al.
2013/0011891 A1    1/2013 Burk et al.

FOREIGN PATENT DOCUMENTS

WO    WO 2015/126221    8/2015

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Kanao et al. (Characterization of isocitrate dehydrogenase from the green sulfur bacterium Chlorobium limicola., Eur. J. Biochem. 269, 1926-1931 (2002).*
International Search Report and the Written Opinion Dated Jun. 24, 2015 From the Korean Intellectual Property Office Re. Application No. PCT/KR2015/001743 and Its Translation of Search Report Into English.
Notice of Reason for Rejection Dated Aug. 18, 2015 From the Korean Intellectual Property Office Re. Application No. 10-2014-0021442.
Notice of Reason for Rejection Dated Apr. 27, 2016 From the Korean Intellectual Property Office Re. Application No. 10-2014-0021442.
Notice of the Reason for Rejection Dated Aug. 18, 2016 From the Korean Intellectual Property Office Re. Application No. 10-2014-0021442.
Levican et al. "Comparative Genomic Anlaysis of Carbon and Nitrogen Assimilation Mechanisms in Three Indigenous Bioleaching Bacteria: Predictions and Validations", BMC Genomics, 9(581): 1-19, Dec. 3, 2008. Abstract, Fig.1.
Bar-Even et al. "Design and Analysis of Synthetic Caton Fixation Pathways", Proc. Natl. Acad. Sci. USA, PNAS, XP002638327, 107(19): 8889-8894, May 11, 2010.

* cited by examiner

*Primary Examiner* — Iqbal H Chowdhdury

(57) ABSTRACT

The present invention relates to a novel carbon dioxide fixation cycle synthesizing a carbohydrate product from carbon dioxide in vitro. In addition, the present invention relates to a unit or a composition carrying out carbon dioxide fixation in cyclic manner. Additionally, the present invention relates to a method to fix carbon dioxide or a method to produce glyoxylate from the carbon dioxide fixation cycle. The present carbon dioxide fixation cycle is not found in natural world, and we found that, when the novel carbon dioxide fixation cycle is used, only three ATP molecules are consumed to fix one carbon dioxide molecule, and thus novel carbon dioxide fixation cycle has an energy conversion efficiency approximately 2.5 times higher than that of the Calvin cycle.

13 Claims, 7 Drawing Sheets
Specification includes a Sequence Listing.

Fig 6

| Reactions | Properties | Isocitrate dehydrogenase |
|---|---|---|
| Decarboxylation (pH 8.5) | $K_m$ (mM) | |
| | Isocitrate | 0.023 |
| | NADP$^+$ | 0.017 |
| | $V_{max}$ (U/mg$^{-1}$) | 94.5 |
| | $k_{cat}$ (s$^{-1}$) | 1.3 × 10$^2$ |
| Carboxylation (pH 7.0) | $K_m$ (mM) | |
| | 2-oxoglutarate | 0.61 |
| | NADPH | 0.013 |
| | NaHCO$_3$ | 0.77 |
| | $V_{max}$ (U/mg$^{-1}$) | 32.5 |
| | $k_{cat}$ (s$^{-1}$) | 4.5 × 10 |

CARBON FIXATION CYCLE AND USE THEREOF

RELATED APPLICATIONS

This application is a National Phase of PCT Patent Application No. PCT/KR2015/001743 having International filing date of Feb. 24, 2015, which claims the benefit of priority of Korean Patent Application No. 10-2014-0021442 filed on Feb. 24, 2014. The contents of the above applications are all incorporated by reference as if fully set forth herein in their entirety.

FIELD AND BACKGROUND OF THE INVENTION

The present invention relates to a novel carbon dioxide fixation cycle and a method for fixing carbon dioxide using the same.

Modern industry has the structure in which most source materials and chemical energy are derived from fossil fuels. However, fossil fuel reserves are finite, and the extensive use of fossil fuels causes serious environmental problems such as the increase in carbon dioxide concentration in air. Elevated carbon dioxide concentration in air has been pointed out as a main cause of global warming. To solve such problems, various types of research and development are being conducted to chemically collect or biologically fix carbon dioxide, which would result in reduction of carbon dioxide of atmosphere. In particular, since sunlight is an ultimate energy source on which humankind depends, light energy conversion by photosynthesis and carbon dioxide ($CO_2$ fixation) fixation should be improved and developed further. The improved $CO_2$ fixation, which may use less adenosine triphosphate (ATP) and reduced nicotinamide adenine dinucleotide phosphate (NADPH), can be more efficiently applied to produce much more carbonaceous products.

Carbon dioxide fixation occurs in plants, algae and various microorganisms. Up to now, there are six carbon dioxide fixation cycles on Earth (Berg. 2011. *Appl Environ Mirobiol.* 77: 1925-1936). A cycle referred to as a Calvin cycle in which rubisco enzyme (ribulose-1,5-bisphosphate carboxylase/oxygenase) works is best known among these carbon dioxide fixation cycles. Calvin cycle is present in living bodies in which oxygenic photosynthesis takes place, including plants, algae, and cyanobacteria, and are also widely distributed in purple non-sulfur bacteria and non-photosynthetic bacteria, in which anoxygenic photosynthesis takes place. In Calvin cycle three carbon dioxide molecules are fixed to synthesize one glyceraldehyde-3-phosphate. This process requires eight ATP molecules to fix one carbon dioxide molecule, the amount of which is calculated based on 2.5 ATP yield from one NADPH. Rubisco has a very low enzymatic turnover number ($K_{cat}$) of 1 to 12 $s^{-1}$. This problem is overcome by increasing an expression level of rubisco in plants so that the enzyme accounts for approximately 50% of water-soluble proteins in chloroplasts. Therefore, efforts have been made to improve kinetic parameters of rubisco in order to enhance light energy utilization efficiency, but did not yet come to fruition.

Reductive citric acid cycle is a process that proceeds in an opposite direction of a citric acid cycle and in which two carbon dioxide molecules are fixed to synthesize one acetyl coenzyme A (acetyl-CoA). This pathway was first found in green sulfur bacteria including *Chlorobium tepidum*. In this carbon dioxide fixation cycle, a 2-oxoglutarate synthase and isocitrate dehydrogenase have an ability to fix carbon dioxide, and they consume 5.5 ATP molecules (the amount of ATP is calculated as described above) to fix one carbon dioxide molecule.

Reductive acetyl-CoA cycle is also referred to as a Wood-Ljungdahl pathway, and was first found in *Clostridia* sp., that is, *Moorella thermoacetica*. This carbon dioxide fixation cycle fixes two carbon dioxide molecules to synthesize acetyl-CoA. In this process, six ATP molecules (the amount of ATP is calculated as described above) are consumed to fix one carbon dioxide molecule.

A 3-hydroxypropionate cycle is present in *Chloroflexus aurantiacus* that is a green non-sulfur bacterium. This carbon dioxide fixation cycle fixes three carbon dioxide molecules to synthesize pyruvate. In this process, seven ATP molecules (the amount of ATP is calculated as described above) are consumed to fix one carbon dioxide molecule. A modified 3-hydroxypropionate cycle referred to as a 3-hydroxypropionate/4-hydroxybutyrate cycle is present in *Archaea* sp. such as *Metallosphaera sedula*, and another modified 3-hydroxypropionate cycle referred to as a dicarboxylate/4-hydroxybutyrate cycle is also found in *Archaea* sp. such as *Ignicoccus hospitalis*. These two carbon dioxide fixation cycles commonly fix two carbon dioxide molecules to synthesize acetyl-CoA. In both processes, seven ATP molecules (the amount of ATP is calculated as described above) are consumed to fix one carbon dioxide molecule.

The contents described as the background art are merely provided to help in understanding the background of the present invention, and thus it should not be taken as an admission that they correspond to the conventional art already known to those of ordinary skill in the related art.

SUMMARY OF THE INVENTION

The present inventors have attempted to establish a novel carbon dioxide fixation cycle that can overcome low energy efficiency of conventional carbon dioxide fixation cycles, so this novel cycle is more efficient than the conventional ones. The present inventors have proposed a new carbon dioxide fixation cycle that works in vitro. This cycle consists of a total 4 enzymes and is not present in the natural world, and we designed a specific application method in which the cycle is induced to fix carbon dioxide, considering thermodynamic characteristics of the four enzyme reactions. The present inventors have found that, when only ATP and NADPH are supplied as biochemical energy to the carbon dioxide fixation cycle, carbohydrates can be continuously produced without providing an additional substrate except a substrate provided at the beginning. Therefore, the present invention has been completed based on these facts.

Therefore, an objective of the present invention is directed to provide a novel carbon fixation cycle to produce a carbohydrate from carbon dioxide molecules.

Another objective of the present invention is directed to provide a unit for carrying out carbon dioxide fixation, which includes the enzymes for carbon fixation cycle.

Still another objective of the present invention is directed to provide a composition for fixing carbon dioxide and preparing a carbohydrate, which includes the carbon fixation cycle.

Yet another objective of the present invention is directed to provide a method for fixing carbon dioxide using the carbon fixation cycle.

Yet another objective of the present invention is directed to provide a method for producing glyoxylate using the carbon fixation cycle.

Other objects and advantages of the present invention will be more clearly described with reference to the detailed description, claims, and drawings of the present invention.

According to an aspect of the present invention, the present invention provides a novel carbon dioxide fixation cycle to produce a carbohydrate.

The present inventors have attempted to establish a novel carbon dioxide fixation cycle that can overcome low energy efficiency of conventional carbon dioxide fixation cycles and is more efficient than the conventional carbon dioxide fixation cycles. As a result, the present inventors have succeeded in establishing a new carbon dioxide fixation cycle that consists of only 4 enzymes and is not present in the natural world, and found that, when the novel carbon dioxide fixation cycle is used, only three ATP molecules (the amount of ATP is calculated as described above) are consumed to fix one carbon dioxide molecule, and thus novel carbon dioxide fixation cycle has a energy conversion efficiency approximately 2.5 times higher than that of the Calvin cycle.

According to a preferred embodiment of the present invention, the carbon fixation cycle of the present invention includes succinyl-CoA synthetase, 2-oxoglutarate synthase, isocitrate dehydrogenase, and isocitrate lyase.

The term "carbon dioxide fixation ($CO_2$ fixation)" used in the present invention refers to a chemical reaction in which inorganic carbon dioxide is converted into organic matter composed of two carbon molecules, using biochemical energy such as ATP and NADPH. All six $CO_2$ fixation cycles in nature fix carbon dioxide by a series of cyclic enzymatic reactions.

The term "biochemical energy" used in the present invention refers to energy possessed by a compound which is involved in the maintenance and transfer of chemical energy generated in living body during a process such as a light reaction of photosynthesis, or respiration. The compound includes at least one compound selected from the group consisting of ATP, NADH and NADPH, reduced ferredoxin, etc.

According to a preferred embodiment of the present invention, succinyl-CoA synthetase constituting the carbon fixation cycle of the present invention converts succinate into succinyl-CoA, the 2-oxoglutarate synthase converts succinyl-CoA into 2-oxoglutarate, isocitrate dehydrogenase converts 2-oxoglutarate into isocitrate, and the isocitrate lyase converts isocitrate into succinate and glyoxylate.

In addition to the six carbon dioxide fixation cycles actually present in nature, there have been attempts to artificially establish carbon fixation cycles. Practically, such attempts were not successful because thermodynamic problems were not realized or solved. Therefore, to establish and operate an efficient carbon dioxide fixation cycle in vitro, relative levels of substrates and products of enzyme reactions have to be considered for the product-favored operation of cyclic reaction, and the corresponding application methods also have to be provided to overcome the low thermodynamic tendency of the enzyme reaction(s) constituting the carbon fixation cycle.

In the present invention, we considered thermodynamic characteristics of the enzymes constituting the novel carbon dioxide fixation cycle, and a specific method is provided to efficiently produce glyoxylate ($C_2$) from 2 carbon dioxide molecules. A value $\Delta_r G'$ (KJ/mol) of each enzymatic reaction is Gibbs energy of the reaction, which is used to indicate thermodynamic characteristics of reaction. When the $\Delta_r G'$ value is less than 0, a forward enzyme reaction may be evaluated to be thermodynamically favorable. On the other hand, the value $\Delta_r G'^\circ$ is the standard free energy change reflecting the equilibrium constant under the standard condition, in which all substrates and products were initially present at 1 M. In fact, $\Delta_r G'$ has to be considered in in vitro reactions because the levels of substrates and products are varied far from 1 M. A series of four enzymatic reactions proceeds to constitute carbon dioxide fixation cycle, so a product of one enzyme reaction becomes the substrate of the next enzyme. By adjusting the concentration of various reaction components including substrates and products, $\Delta_r G'$ reflecting the thermodynamic characteristics of actual reactions may be reduced to 0 or less. As a result, the carbon dioxide fixation cycle can be directed to fix carbon dioxide producing glyoxylate.

FIG. 2 shows the thermodynamic calculation results of the four enzyme reactions according to the levels of substrates and products of the reactions constituting the new carbon fixation cycle. Based on results, the reaction mixture in which the carbon dioxide fixation cycle is directed to fix carbon dioxide refers to a condition in which levels of the succinate and/or succinyl-CoA are maintained at a higher level than those of 2-oxoglutarate and/or isocitrate. Since succinate dehydrogenase keeps the reaction equilibrium shifted toward a direction to form succinyl-CoA from succinate, the succinate supplied to reaction mixture is easily converted into succinyl-CoA. However, since 2-oxoglutarate synthase and isocitrate dehydrogenase keep the reaction equilibrium shifted toward a direction in which decarboxylation reaction favors, 2-oxoglutarate and isocitrate that are products of forward reactions (substrates of reverse reactions at the same time) should be maintained at low concentration to prevent reverse decarboxylation reactions. To fix carbon dioxide easily while maintaining low level of 2-oxoglutarate, it may be desirable to use the isocitrate dehydrogenase, which has a characteristic of having a high substrate affinity (low $K_m$ value) for 2-oxoglutarate, and also has a characteristic of having a high rate constant (high $K_{cat}$ value). Finally, since the isocitrate lyase keeps the reaction equilibrium highly shifted toward a direction to form succinate and glyoxylate from isocitrate, this reaction leads to the maintenance of low level of isocitrate. As a result, the entire reaction is not suppressed even when the succinate level is kept at high level.

When the relationship between the concentration of substrate and product is summed up, it is desirable to maintain the succinate level higher than that of succinyl-CoA. More preferably, the concentrations of succinate and succinyl-CoA are maintained at a ratio 2:1 to 100:1, and most preferably at a ratio of approximately 10:1. For example, when the concentration of succinate is in a range of 1 mM to 100 mM, the concentration of succinyl-CoA is most preferably maintained in a range of 0.1 mM to 10 mM. When concentration of succinyl-CoA is less than this range, carboxylation rate of 2-oxoglutarate synthase is not saturated, and thus optimum reaction conditions may not be provided. When concentration of succinyl-CoA exceeds this range, optimum reaction conditions may not be provided for reasons such as non-specific inhibition of enzyme reactions constituting the carbon dioxide fixation cycle.

Also, the concentration of succinyl-CoA is preferably maintained at a higher level than that of 2-oxoglutarate. More preferably, the concentrations of succinyl-CoA and 2-oxoglutarate are maintained at a ratio of 100:1 to 10,000:1, and most preferably at a ratio of approximately 1,000:1. For example, when the concentration of succinyl-CoA is in a range of 0.1 mM to 10 mM, the concentration of the 2-oxoglutarate is most preferably maintained in a range of 0.1 μM to 10 μM.

When the concentration of 2-oxoglutarate is less than this range, the carboxylation rate of isocitrate dehydrogenase is not saturated, and thus the optimum reaction conditions may not be provided. When the concentration of the 2-oxoglutarate exceeds this range, the optimum reaction conditions may not be provided for reasons such as non-specific inhibition of enzyme reactions constituting the carbon dioxide fixation cycle.

The concentration of 2-oxoglutarate is preferably maintained higher than that of isocitrate. More preferably, the concentrations of 2-oxoglutarate and isocitrate are maintained at a ratio of 2:1 to 100:1, and most preferably at a ratio of approximately 10:1. For example, when the concentration of the 2-oxoglutarate is in a range of 1 µM to 1 mM, the concentration of isocitrate is most preferably maintained in a range of 0.1 µM to 0.1 mM.

Since isocitrate lyase keeps the reaction equilibrium highly shifted toward a direction to form succinate and glyoxylate from isocitrate as a substrate, the reaction proceeds even when the isocitrate is present at concentration lower than those of succinate and/or glyoxylate. In this case, the concentrations of isocitrate and glyoxylate are preferably maintained at a ratio of 1:10 to 1:1,000, and more preferably approximately at a ratio of 1:100. For example, when the concentration of isocitrate is in a range of 1 µM to 1 mM, the concentration of glyoxylate is most preferably maintained at 10 mM or less.

The proper concentration ratio between the substrate and product may vary depending on the concentration of carbon donors (carbonate ions ($CO_3^{2-}$, carbon dioxide ($CO_2$), electron donors, ATP, and coenzyme A (CoA), etc.

For example, the carbon dioxide fixation cycle is directed to fix carbon dioxide, when carbon donors (carbonate ions ($CO_3^{2-}$), carbon dioxide ($CO_2$), etc.), which are substrates of 2-oxoglutarate synthase and isocitrate dehydrogenase, are present at high levels. In FIG. 2, although it is assumed that concentration of dissolved carbon dioxide is 1 mM, various known techniques are applicable to enhance the solubility of carbon dioxide, which leads to the product-favored reactions of enzymes. Still another condition in which the carbon dioxide fixation cycle is directed to fix carbon dioxide is to keep glyoxylate at low level. In particular, when carbon dioxide fixation cycle is applied in vitro, rapid removal of the produced glyoxylate from reaction mixture would remarkably enhance the entire reactions. A known technique for acquiring glyoxylate (U.S. Pat. No. 3,998,878) may be used to remove glyoxylate from reaction mixture. Also, yet another condition in which the carbon dioxide fixation cycle is directed to fix carbon dioxide is to keep a high concentration ratio of NADPH to $NADP^+$, a high concentration ratio of ATP to ADP, and a high concentration ratio of succinyl-CoA to coenzyme A. High concentration ratio of ATP to ADP eventually leads to the product-favored reaction of succinyl-CoA synthetase to increase succinyl-CoA and reduce coenzyme A. Therefore, if ATP and NADPH are continuously regenerated from ADP and $NADP^+$, respectively, the forward reactions of the cycle may be remarkably enhanced.

In the present invention, 2-oxoglutarate synthase and isocitrate dehydrogenase are able to fix carbon dioxide molecules, forming isocitrate. Isocitrate lyase decomposes isocitrate into succinate and glyoxylate. Also, succinyl-CoA synthetase provides succinyl-CoA, a substrate of 2-oxoglutarate synthase, and cycle goes on and on. Since succinate is again used as a substrate of the succinyl-CoA synthetase, succinate is added to the reaction mixture at the beginning of cyclic reaction only; we do not need to add more succinate during the operation of carbon dioxide fixation cycle; one glyoxylate molecule is continuously formed from two carbon dioxide molecules while other carbohydrate metabolic intermediates are being maintained at constant levels.

A method for acquiring the four enzymes constituting the carbon fixation cycle of the present invention is not limited, but enzymes and genes coding for the enzymes may be preferably isolated from microorganisms that can produce the enzymes.

In the present invention, a target for securing a gene of 2-oxoglutarate synthase is not limited. However, according to a preferred embodiment of the present invention, the 2-oxoglutarate synthase is isolated from at least one strain selected from the group consisting of green sulfur bacteria, and chemolithotroph. The green sulfur bacteria are photosynthetic bacteria belonging to Chlorobi phylum in a taxonomical aspect, and may include bacteria such as *Ancalochloris* sp., *Chlorobium* sp., *Chlorobaculum* sp., *Pelodictyon* sp., *Chloroherpeton* sp., *Clathrochloris* sp., *Prosthecochloris* sp., *Ignavibacterium* sp., *Melioribacter* sp., etc. Also, chemolithotrophs are bacteria belonging to Aquificae phylum in a taxonomical aspect, and may include bacteria such as genus *Thermosulfidibacter*, genus *Aquificaceae* including *Hydrogenobacter* sp., *Aquifex* sp., etc., genus *Hydrogenothermaceae* including *Persephonella* sp., *Sulfurihydrogenibium* sp., etc., and the genus *Desulfurobacteriaceae* including *Desulfobacterium* sp., etc.

A TCA cycle enzyme, α-ketoglutarate dehydrogenase is a bidirectional enzyme so it may produce 2-oxoglutarate through carboxylation reaction. Therefore, α-ketoglutarate dehydrogenase may be used instead of 2-oxoglutarate synthase. However, the $K_m$ of α-ketoglutarate dehydrogenase for $CO_2/HCO_3^-$ is not sufficiently lower than that for α-ketoglutarate. Accordingly, it is difficult to use the α-ketoglutarate dehydrogenase for the purpose of fixing carbon dioxide without improving the carboxylation activity of the enzyme.

In the present invention, a target for securing the isocitrate dehydrogenase or a gene thereof is not also limited. For example, the isocitrate dehydrogenase or the gene thereof may be secured from the chemolithotroph, or the photosynthetic bacteria such as green sulfur bacteria, green non-sulfur bacteria, purple sulfur bacteria, purple non-sulfur bacteria, cyanobacteria, etc.

According to a preferred embodiment of the present invention, the carbon fixation cycle of the present invention may be constructed by enzymes, which are purified through the overexpression of genes encoding enzymes in *Escherichia coli* (*E. coli*). Genes encoding for the four enzymes are cloned into expression vector and they are expressed using expression system of *E. coli*. The codon optimization of the DNA encoding enzymes may be required for their better expression in *E. coli*.

According to another aspect of the present invention, the present invention provides a unit for carrying carbon dioxide fixation, which includes the carbon fixation cycle.

According to still another aspect of the present invention, the present invention provides composition of reaction mixture for fixing carbon dioxide and preparing a carbohydrate, which initiates the cyclic reaction.

The "unit for carrying carbon dioxide fixation" used in the present invention refers to the reaction mixture that can carry out carbon dioxide fixation. Such units may be combined into larger assembly.

The unit or mixture composition of the present invention may include a proper concentration of buffer, salt, cofactor, substrates, and electron donor, all of which are required for enzymatic fixation of carbon dioxide.

The term "photosynthetic light reaction product" used in the present invention refers to a product that is produced by carrying out light reaction in which photosynthetic bacteria convert light into chemical energy. Here, the product includes at least one light reaction product selected from the group consisting of adenosine triphosphate (ATP), nicotinamide adenine dinucleotide (NADH), and nicotinamide adenine dinucleotide phosphate (NADPH).

The term "biochemical energy" used in the present invention refers to energy possessed by a compound which is involved in the maintenance and transfer of chemical energy generated in living system during a process such as light reaction of photosynthesis, or respiration. Here, the compound includes at least one compound selected from the group consisting of ATP, NADH, NADPH, and ferredoxin, etc.

The present invention is designed to provide a unit or composition to carry out carbon dioxide fixation, which includes 2-oxoglutarate synthase and isocitrate dehydrogenase, succinyl-CoA synthetase and isocitrate lyase. This mixture constitutes cyclic reaction to fix carbon dioxide, and this cycle is not present in nature. Here, the unit or composition includes the four enzymes, and additives required for four enzyme reactions to fix carbon dioxide.

FIG. 1 is a diagram schematically showing a novel carbon fixation cycle which includes succinyl-CoA synthetase, 2-oxoglutarate synthase, isocitrate dehydrogenase, and isocitrate lyase. Two carbon dioxide ($CO_2$) molecules are consumed during consecutive reactions of the cycle to produce one glyoxylate molecule. In this process, one ATP molecule and two NADPH molecules are consumed. All other materials except ATP and NADPH are regenerated and reused through a series of enzymatic reactions of the carbon fixation cycle In the present invention, the 2-oxoglutarate synthase may carry out carboxylation in which one carbon dioxide is added to substrate, and also carry out a decarboxylation in which one carbon dioxide molecule is removed from substrate. Little is known about the enzymatic characteristics of 2-oxoglutarate synthase. Therefore, carboxylation and decarboxylation characteristics of 2-oxoglutarate synthase need to be examined in detail.

FIG. 3 shows carboxylation and decarboxylation activities of an isolated 2-oxoglutarate synthase at pH 7.0. As a result, 2-oxoglutarate synthase carries out carboxylation using succinyl-CoA as a substrate, and has reaction rate of approximately 0.9 μmole/min·mg protein. The enzyme also mediates decarboxylation in the presence of the 2-oxoglutarate, and has a reaction rate of approximately 6.0 μmole/min·mg protein. Therefore, 2-oxoglutarate synthase has a relatively higher decarboxylation rate as compared with carboxylation rate. The enzyme carries out carboxylation (carbon fixation) when 2-oxoglutarate level is maintained at lower than that of succinyl-CoA.

According to a preferred embodiment of the present invention, the composition of the present invention may further include a reduced ferredoxin to promote carbon fixation activity of 2-oxoglutarate synthase, and may also include a ferredoxin reductase to reduce ferredoxin using NADPH.

As shown in FIG. 3, ferredoxin is used for carbon fixation reaction of 2-oxoglutarate synthase, and NADPH is used as an electron donor to reduce ferredoxin. However, the type of the electron donor may also be readily selected from NADPH, NADH or pyruvate, and applied according to the type of ferredoxin used and the ferredoxin reductase by those skilled in the related art. Therefore, the composition of the present invention may further include at least one electron donor selected from the group consisting of reduced nicotinamide adenine dinucleotide phosphate (NADPH), reduced nicotinamide adenine dinucleotide (NADH), and pyruvate to promote the carbon fixation activity of 2-oxoglutarate synthase. Also, ferredoxin:nicotinamide adenine dinucleotide phosphate reductase (ferredoxin:$NADP^+$ reductase), ferredoxin:nicotinamide adenine dinucleotide reductase (ferredoxin:$NAD^+$ reductase), and ferredoxin:pyruvate reductase may be applied as the ferredoxin reductase usable in the present invention.

According to a preferred embodiment of the present invention, the composition of the present invention may further include at least one carbon donor selected from the group consisting of carbonate ions ($CO_3^{2-}$), and carbon dioxide ($CO_2$) for carbon fixation activity of 2-oxoglutarate synthase.

The carbonate ion ($CO_3^{2-}$) may be dissociated from various compounds, or it may be directly derived from dissolved carbon dioxide in an aqueous solution. Preferably, the carbonate ions ($CO_3^{2-}$) may be dissociated from carbonic acid ($H_2CO_3$), sodium hydrogen carbonate ($NaHCO_3$), sodium carbonate ($Na_2CO_3$), and calcium carbonate ($CaCO_3$), etc.

Also, since 2-oxoglutarate synthase has a characteristic to carry out carboxylation even at low concentration of carbon dioxide, the enzyme may sufficiently carry out reaction in the presence of $CO_2$ at an atmospheric level (0.03% to 0.05%), or $CO_2$ may be supplied at concentration greater than the atmospheric level to promote the forward reaction.

In the present invention, the optimum concentrations of succinyl-CoA and sodium hydrogen carbonate ($NaHCO_3$) to fix carbon dioxide and produce glyoxylate were determined using 2-oxoglutarate synthase. An upper panel of FIG. 4 shows results of carrying out a carboxylation reaction of 2-oxoglutarate synthase at varying concentrations of succinyl-CoA. In this reaction, sodium hydrogen carbonate is provided at saturation level. Carboxylation rate of 2-oxoglutarate synthase is saturated when succinyl-CoA is added at concentration of approximately 0.1 mM or more. A lower panel of FIG. 4 shows results of carrying out a carboxylation reaction of 2-oxoglutarate synthase at varying concentration of sodium hydrogen carbonate. In this reaction, succinyl-CoA is provided at saturation level. Carboxylation rate of 2-oxoglutarate synthase is saturated when sodium hydrogen carbonate is added at concentration of approximately 5 mM or more. Since 2-oxoglutarate synthase has a characteristic of carrying out carboxylation reaction even at relatively low carbon dioxide concentration, the composition of reaction mixture includes a carbonate or sodium hydrogen carbonate. It is possible to use various compounds having a property of dissociating the carbonate in an aqueous solution, or to use carbon dioxide itself after carbon dioxide is dissolved in an aqueous solution. In this case, the optimum carbon dioxide source and the use thereof may be determined according to the purpose of research and development by those skilled in the art.

Also, the concentration of carbonate ions ($CO_3^{2-}$) for carboxylation reaction of 2-oxoglutarate synthase is preferably in a range of 50 μM to 500 mM, and more preferably in a range of 1 mM to 100 mM. When the concentration of carbonate ions is less than this range, the carboxylation rate of 2-oxoglutarate synthase is not saturated, and thus the optimum reaction may not occur. On the other hand, when the concentration of sodium hydrogen carbonate exceeds this range, the optimum reaction may not occur because hydrogen ion concentration (pH) of the reaction mixture may be changed largely.

The hydrogen ion concentration (pH) suitable for 2-oxoglutarate synthase reaction of the present invention is not limited, but preferably in a range of 5 to 9, more preferably in a range of 6 to 8.

FIG. 5 shows bidirectional enzyme activities of isocitrate dehydrogenase according to change in hydrogen ion concentration of reaction mixture. An upper panel of the drawing shows carboxylation reaction rate of isocitrate dehydrogenase in the presence of 2-oxoglutarate at varying pHs. As a result, isocitrate dehydrogenase has the optimum carbon fixation activity at neutral pH 7.0. Lower panel of the drawing shows decarboxylation reaction rate of isocitrate dehydrogenase in the presence of isocitrate at varying pHs. As a result, isocitrate dehydrogenase has the optimum decarboxylation activity at a weakly basic pH 8.5. These results suggest that carbon fixation using isocitrate dehydrogenase derived from *C. tepidum* readily may occur at neutral pH condition since the enzyme has a relatively lower decarboxylation activity at pH 7.0.

According to a preferred embodiment of the present invention, the composition of the present invention may further include at least one electron donor selected from the group consisting of reduced nicotinamide adenine dinucleotide phosphate (NADPH), and reduced nicotinamide adenine dinucleotide (NADH) for the carbon fixation activity of isocitrate dehydrogenase.

FIG. 6 shows results of kinetic parameters of isocitrate dehydrogenase obtained from reactions at pH 7.0 and pH 8.5, which are the optimum pHs for carboxylation and decarboxylation reactions, respectively. As a result, the enzyme carries out carboxylation reaction using 2-oxoglutarate and sodium hydrogen carbonate as substrates and NADPH as electron donor, and thus has the reaction rate of approximately 33 µmole/min·mg protein. Also, isocitrate dehydrogenase carries out decarboxylation reaction using isocitrate as substrate and $NADP^+$ as electron accepter, and thus has the reaction rate of approximately 95 µmole/min·mg protein. NADPH is used to carry out the carboxylation of isocitrate dehydrogenase of *C. tepidum*. However, it is also possible to use NADH as still another type of electron donor to carry out the optimum reaction, depending on the origin of isocitrate dehydrogenase. It was revealed that isocitrate dehydrogenase from *C. tepidum* has a similar substrate affinity for NADPH and $NADP^+$. The $K_m$ value of this enzyme for sodium hydrogen carbonate is 3 times lower than those of isocitrate dehydrogenases from other sources. The results indicate that *C. tepidum*-derived isocitrate dehydrogenase has a higher affinity for carbon dioxide, compared to other conventional isoenzymes. Also, it was revealed that the enzyme has a relatively higher decarboxylation rate, as seen from the rate constant, $K_{cat}$. However, carbon fixation reaction of the enzyme may be directed when isocitrate is maintained at lower level, as compared with that of 2-oxoglutarate. In addition, it is judged that the enzyme may be efficiently used toward fixing carbon dioxide to produce isocitrate when pH of the reaction mixture is maintained at neutral pH.

Also, the concentration of the sodium hydrogen carbonate for the carboxylation reaction of isocitrate dehydrogenase is preferably maintained in a range of 50 µM to 500 mM, more preferably in a range of 1 mM to 100 mM. When the concentration of sodium hydrogen carbonate is less than this range, carboxylation rate of isocitrate dehydrogenase is not saturated, and thus the optimum reaction may not occur. On the other hand, when the concentration of sodium hydrogen carbonate exceeds this range, the optimum reaction may not occur, because decrease in hydrogen ion concentration may affect the reactions of four enzymes constituting the carbon dioxide fixation cycle.

Glyoxylate production through the novel carbon dioxide fixation cycle was examined by using reaction mixture, which includes two subunits of succinyl-CoA synthetase, two subunits of 2-oxoglutarate synthase, isocitrate dehydrogenase, and isocitrate lyase. FIG. 7 shows glyoxylate-production rate by the reaction mixture of four enzymes constituting the novel carbon dioxide fixation cycle. The standard reaction mixture contains enzymes (each at 10 µM), 5 mM succinate, 0.5 mM NADPH, 1 mM ATP, 1 mM coenzyme A, 20 mM magnesium chloride, 12.5 mM glutathione, 20 mM sodium hydrogen carbonate in 100 mM HEPES buffer (pH 7.0). To examine an effect of each reaction component on glyoxylate production, each of succinyl-CoA synthetase, 2-oxoglutarate synthase, isocitrate dehydrogenase, isocitrate lyase, succinate, ATP, NADPH, sodium hydrogen carbonate, and succinate was omitted from standard reaction mixture. As a result, glyoxylate was readily produced only in standard reaction mixture. However, when one of the four enzymes was excluded from the reaction mixture, glyoxylate was hardly produced. Omission of ATP or NADPH from the reaction mixture, glyoxylate was hardly produced, too. Conversely, glyoxylate was still produced at a yield corresponding to approximately 8% of that from the standard reaction mixture after omission of sodium hydrogen carbonate. We assume that glyoxylate was produced, using carbon dioxide dissolved in buffer. This result indicates that the carbon dioxide fixation cycle may be operated to produce glyoxylate even at the same carbon dioxide concentration at an atmospheric level (0.03% to 0.05%; 300 to 500 ppm). In FIG. 7, succinate was used to begin the cyclic reaction to fix carbon dioxide. Similarly, either succinyl-CoA, 2-oxoglutarate, or isocitrate, which are other intermediates of the carbon dioxide fixation cycle, can be used as a starting material of the cyclic reaction, and the optimum starting material and the use thereof may be determined according to the purpose of research and development by those skilled in the art.

According to yet another aspect of the present invention, the present invention provides a method for fixing carbon dioxide, which includes supplying at least one carbon donor selected from the group consisting of carbonate ions ($CO_3^{2-}$) and carbon dioxide ($CO_2$) to the carbon fixation cycle by succinyl-CoA synthetase, 2-oxoglutarate synthase, isocitrate dehydrogenase, and isocitrate lyase.

When this fixation method is used, a carbohydrate, preferably glyoxylate, may be efficiently produced from carbon donors such as carbonate ions or carbon dioxide using the energy level, which is much lower than those of the fixation methods known in the prior art.

According to a preferred embodiment of the present invention, the fixation method may use one adenosine triphosphate (ATP) molecule and two reduced nicotinamide adenine dinucleotide phosphate (NADPH) molecules as the biochemical energy to fix two carbon dioxide molecules.

The fixation method of the present invention may further include steps to isolate succinyl-CoA synthetase, 2-oxoglutarate synthase, isocitrate dehydrogenase and isocitrate lyase.

Also, the fixation method of the present invention may further include steps adding one substrate (at least one carbohydrate selected from the group consisting of succinate, succinyl-CoA, 2-oxoglutarate and isocitrate) and biochemical energy sources (all of ATP, NADH, NADPH, and reduced ferredoxin, etc.) as starting materials to constitute the carbon fixation cycle.

Since the initially-added substrate is regenerated after each cycle and reused for the next cycle, we do not have to add it again during reaction.

According to yet another aspect of the present invention, the present invention provides a method for producing glyoxylate from at least one carbon donor selected from the group consisting of carbonate ions ($CO_3^{2-}$) and carbon dioxide ($CO_2$) through the carbon fixation cycle, which consists of succinyl-CoA synthetase, a 2-oxoglutarate synthase, isocitrate dehydrogenase, and isocitrate lyase.

The carbon fixation cycle may also be constructed by simply mixing the isolated enzymes in aqueous reaction mixture, but such a method has a problem in that it has only a transient production of glyoxylate. As glyoxylate is accumulated in reaction mixture, a $\Delta_r G'$ (KJ/mol) value of isocitrate lyase reaction also increases. Then, isocitrate lyase reaction to form glyoxylate may be hampered. Glyoxylate may be purified by the known method using methanol and urea from reaction mixture to drive the isocitrate reaction forwardly. However, all enzymes of the carbon dioxide fixation cycle may be damaged during glyoxylate purification. Accordingly, enzymes may be kept intact separately during recovery of glyoxylate by a method of cross linking of enzymes under ultraviolet rays to solid surface, by a method of binding of enzymes using immobilized antibodies on solid surface, or by a method of linking enzymes to the solid surface using ligand and receptor.

The characteristics and advantages of the present invention are summarized, as follows:

(1) The present invention provides a novel carbon dioxide fixation cycle to form carbohydrate.

(2) Also, the present invention provides a unit or composition of reaction mixture to carry out carbon dioxide fixation through carbon dioxide fixation cycle.

(3) In addition, the present invention provides a method for fixing carbon dioxide or producing glyoxylate using the carbon dioxide fixation cycle.

(4) When the novel carbon dioxide fixation cycle according to the present invention is used, only three ATP molecules (the amount of which is calculated by converting 1 NADPH into 2.5 ATP molecules) are consumed to fix one carbon dioxide molecule. Therefore, this carbon dioxide fixation cycle has the highest energy conversion efficiency, compared to other carbon dioxide fixation cycles known to be present on Earth. If this novel carbon dioxide fixation cycle is operated in vitro, energy is not required for cell maintenance and other metabolic processes. Accordingly, the chemical energy from light reaction of photosynthesis can be used exclusively to fix carbon dioxide. Therefore, the energy conversion efficiency would be remarkably enhanced. Further, this novel carbon dioxide fixation cycle has an advantage in that, when a substrate of any enzyme of cycle is added once at the beginning, subsequently persistent production of glyoxylate may be possible.

BRIEF DESCRIPTION OF THE SEVERAL VIEWS OF THE DRAWINGS

FIG. 2A shows the delta free-energy profile of succinyl-CoA synthetase reaction according to the relative levels of succinate and succinyl-CoA which are the substrate and product of succinyl-CoA synthetase, respectively. We also assumed that CoA is present at 1 mM and the relative mole ratio of ATP and ADP is 1. FIG. 2B shows the delta free-energy profile of 2-oxoglutarate synthase reaction according to the relative levels of succinyl-CoA and 2-oxoglutarate which are the substrate and product of 2-oxoglutarate synthase, respectively. It is assumed that the concentration of dissolved carbon dioxide is 1 mM; molar ratio of NADPH to $NADP^+$ is 100; concentration ratio of succinyl-CoA to coenzyme A is 10. FIG. 2C shows the delta free-energy profile of isocitrate dehydrogenase reaction according to the relative levels of 2-oxoglutarate and isocitrate which are the substrate and product of isocitrate dehydrogenase, respectively. It is assumed that the concentration of dissolved carbon dioxide is 1 mM; mole ratio of NADPH to $NADP^+$ is 100. FIG. 2D shows the delta free-energy profile of isocitrate lyase reaction according to the relative levels of isocitrate and glyoxylate which are the substrate and product of isocitrate lyase, respectively. Calculations and predictions were made assuming that the level of succinate, which is another product of isocitrate lyase reaction and a substrate of succinyl-CoA synthetase as well, is 10 mM.

FIG. 6 shows the kinetic parameters for decarboxylation and carboxylation of isocitrate dehydrogenase at optimum pH values of each reaction. Isocitrate and $NADP^+$ were used as substrates for decarboxylation reaction, whereas 2-oxoglutarate, NADPH and sodium hydrogen carbonate (NaHCO$_3$) were used as substrates for carboxylation reaction.

DESCRIPTION OF SPECIFIC EMBODIMENTS OF THE INVENTION

Figure 1:
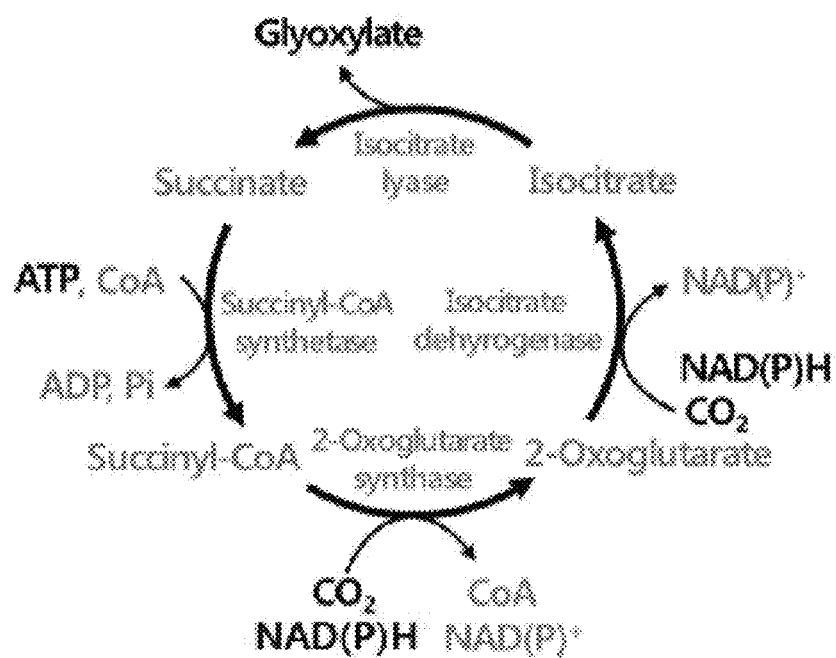
FIG. 1 is a diagram schematically showing a novel carbon fixation cycle which is operated by the activities of succinyl-CoA synthetase, 2-oxoglutarate synthase, isocitrate dehydrogenase, and isocitrate lyase. Two carbon dioxide ($CO_2$) molecules are fixed by the consecutive reactions of the enzymes to produce one glyoxylate molecule. In this process, one ATP molecule and two NADPH molecules are consumed. All metabolic intermediates of this novel carbon fixation cycle except ATP and NADPH may be regenerated through a series of enzymatic reactions.
Figure 2A:
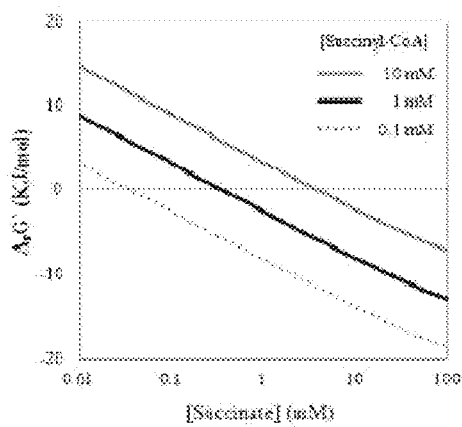
FIGS. 2A, 2B, 2C, and 2D show the favored direction (product-favored or substrate-favored) of enzyme reactions based on thermodynamic calculation at varying levels of substrates and products of four enzymes of carbon fixation cycle. We considered all reactions are performed at pH 7 and the concentrations of all salts other than substrates and products are fixed at 0.1 M.
Figure 2B:
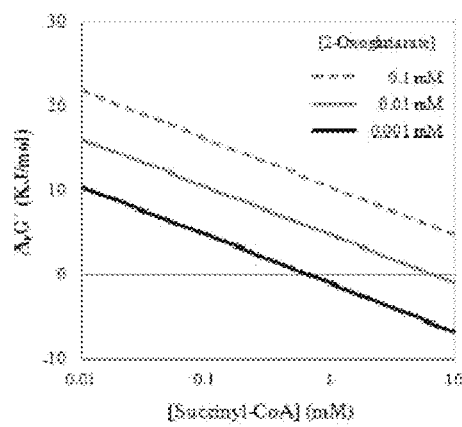
Figure 2C:
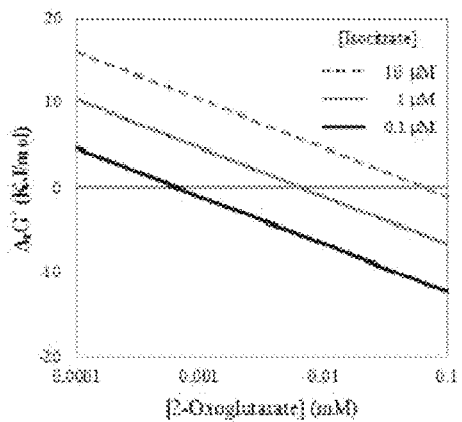
Figure 2D:
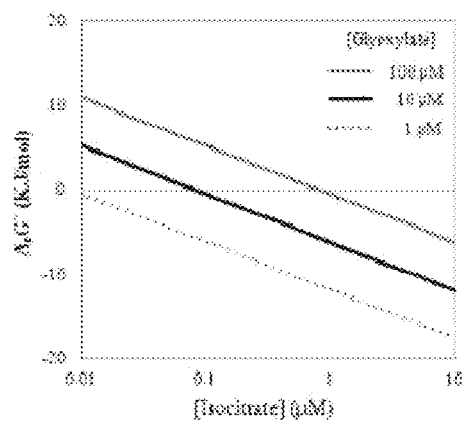

Hereinafter, the present invention will be described in further detail with reference to examples thereof. These examples are merely provided to describe the present invention in further detail, and thus it will be apparent to those skilled in the related art that the examples are not intended to limit the scope of the present invention according to the inventive concept.

EXAMPLES

Example 1: Prediction of Thermodynamic Characteristics of Novel Carbon Fixation Cycle The present invention was designed to prepare the composition of reaction mixture, which leads to the CO$_2$-fixation-favored reaction of the novel carbon dioxide fixation cycle based on the thermodynamic characteristics of enzyme reactions constituting the cycle. $\Delta_r G'$ (KJ/mol) value of each reaction is used as an indicator to determine the thermodynamic characteristics of enzyme reaction, and represents the favored-direction (substrate-favored or product-favored) of reaction. In this case, when the $\Delta_r G'$ value is less than 0, a forward reaction of the enzyme is possible. $\Delta_r G'^{o}$ values under the standard condition, at which all the substrates and products are present at 1 M, are known. However, the direction of actual reactions cannot be predicted based on $\Delta_r G'^{o}$ because the levels of substrate and product are not 1 M. A calculation method (Flamholz et al. 2012. *Nucleic Acids Res.* 40(D1): D770-D775) known to check $\Delta_r G'$ values at varying levels of compositions was used. In this case, all reactions were considered to occur at pH 7.0, and the total concentration of salts other than the substrates and products was fixed at 0.1 M. Since a series of enzymatic reactions by four enzymes works in carbon dioxide fixation cycle, the product of each enzyme reaction becomes a substrate for the next enzyme reaction. Condition at which carbon dioxide fixation cycle operates in a direction to fix carbon dioxide was examined at varying the concentrations of various reaction components including glyoxylate.

FIG. 2 shows the thermodynamic calculation results for the four reactions according to the levels of substrates and products of the reactions constituting the novel carbon fixation cycle. FIG. 2A shows the direction of succinyl-CoA synthetase reaction according to the varying levels of succinate and succinyl-CoA, which are the substrate and product of succinyl-CoA synthetase, respectively. As a result, when succinate was present at level between 1 mM and 100 mM, and succinyl-CoA was present at level between 0.1 mM to 10 mM, the reaction tends to proceed forward. In fact, it was revealed that the reaction was product-favored even when two equivalents of succinyl-CoA were present per one equivalent of succinate. However, because a forward reaction of 2-oxoglutarate synthase, which is the next reaction, may be hindered by CoA at high level, the concentration of succinyl-CoA was preferably adjusted to a range of 0.1 mM to 10 mM. The relative concentration ratio of ATP and adenosine diphosphate (ADP) in this reaction composition was assumed to be 1. When the ratio of ATP to ADP is higher than 1, product-favored reaction is expected. FIG. 2B shows the direction of 2-oxoglutarate synthase reaction at varying levels of succinyl-CoA and 2-oxoglutarate, which are the substrate and product of 2-oxoglutarate synthase, respectively. As a result, when succinyl-CoA was present in a range of 1 mM to 10 mM, a forward reaction was predicted only when 2-oxoglutarate was present in a range of 0.001 mM to 0.01 mM. Accordingly, considering the next reaction, it is desirable to use an isocitrate dehydrogenase having a high $K_{cat}$ value as well as low $K_m$ value (high affinity) for 2-oxoglutarate. It was assumed that the level of dissolved carbon dioxide for reaction was 1 mM, but the forward reaction was more easily predicted when dissolved carbon dioxide was present at levels higher than 1 mM. It was assumed that the ratio of NADPH to NADP$^+$ of the reaction was 100, and the ratio of the succinyl-CoA to CoA was 10, but the thermodynamic preference of the reaction can be easily adjusted by those skilled in the related art by adjusting the ratios of the components of the reaction mixture. FIG. 2C shows the direction of isocitrate dehydrogenase reaction at varying levels of 2-oxoglutarate and isocitrate, which are the substrate and product of isocitrate dehydrogenase, respectively. As a result, when 2-oxoglutarate was present in a range of 0.001 mM to 0.1 mM, a forward reaction was predicted only when isocitrate was present in a range of 0.1 μM to 10 μM. Accordingly, considering the next reaction, it is desirable to use isocitrate lyase having a high $K_{cat}$ value as well as low $K_m$ value (high affinity) for isocitrate. It was assumed that the concentration of dissolved carbon dioxide was 1 mM and the ratio of NADPH to NADP$^+$ was 100, but the thermodynamic preference of the reaction can be easily adjusted by those skilled in the related art by adjusting the concentrations and ratios of the components in reaction mixture. FIG. 2D shows the direction of isocitrate lyase reaction according to the varying levels of isocitrate and glyoxylate, which are the substrate and product of isocitrate lyase, respectively. The level of succinate, which is another product of isocitrate lyase and a substrate of succinyl-CoA synthetase as well, was assumed to be 10 mM. Forward reaction was predicted when isocitrate level was present at a range of 0.1 μM to 10 μM, and glyoxylate at a range of 1 μM to 100 μM. In fact, isocitrate lyase reaction was predicted to proceed forward even when a hundred equivalents of glyoxylate was present per one equivalent of isocitrate. Thus, when the isocitrate is present at 10 μM, a forward reaction is expected until the glyoxylate is present at a concentration of 1 mM. Proper substrate concentrations of four enzymes and glyoxylate also vary depending on the reaction temperature, pH, concentrations of salts and carbon dioxide, relative ratios of NADPH to NADP$^+$, ATP to ADP, and that of succinyl-CoA to CoA, etc. Therefore, it will be apparent to those skilled in the related art that the proper substrate concentrations of four enzymes and glyoxylate used are not limited by the examples of the present invention.

Example 2: Acquisition of Genes Including Carbon Dioxide Fixation Enzymes

Genes of succinyl-CoA synthetase set forth in SEQ ID NOS: 1 and 2, isocitrate lyase set forth in SEQ ID NO: 3, 2-oxoglutarate synthase set forth in SEQ ID NOS: 4 and 5, and isocitrate dehydrogenase set forth in SEQ ID NO: 6 were cloned and expressed in *E. coli* for the purification of the corresponding enzymes. The genes coding for succinyl-CoA synthetase, which is composed of two subunits set forth in SEQ ID NOS: 1 and 2, and the isocitrate lyase set forth in SEQ ID NO: 3 were all isolated from *E. coli*. Histidine tag (His-tag) was linked to the N terminus or C terminus of each of three proteins through polymerase chain reactions using *E. coli* chromosomal DNA as a template. To clone the gene encoding an α-subunit of succinyl-CoA synthetase, a forward primer set forth in SEQ ID NO: 7 and a reverse primer set forth in SEQ ID NO: 8 were used. Here, the forward primer was designed to modify the start ATG codon of protein and insert a BamHI site as well. The reverse primer was designed to insert the HindIII site. To clone the gene encoding the β-subunit of succinyl-CoA synthetase, a forward primer set forth in SEQ ID NO: 9 and reverse primer set forth in SEQ ID NO: 10 were used. Here, the forward primer was designed to modify the start codon of protein and insert the EcoRI site as well. The reverse primer was designed to modify the stop codon and insert the BamHI site as well. To clone the gene of isocitrate lyase, a forward primer set forth in SEQ ID NO: 11 and a reverse primer set forth in SEQ ID NO: 12 were used. Here, the forward primer was designed to modify the start codon of protein and insert the BamHI site as well. The reverse primer was designed to insert HindIII site. All DNA fragments from polymerase chain reaction were cloned into protein expression vector pQE30 (Qiagen) containing a histidine tag. As results, N termini of succinyl-CoA synthetase α-subunit and isocitrate lyase were linked to the histidine tag, and the C terminus of succinyl-CoA synthetase β-subunit was linked to the histidine tag.

The deduced amino acid sequences of 2-oxoglutarate synthase set forth in SEQ ID NOS: 4 and 5 and that of isocitrate dehydrogenase set forth in SEQ ID NO: 6 were obtained from the genome of green sulfur bacterium, *C. tepidum*. The base sequences of 2-oxoglutarate synthase and isocitrate dehydrogenase were optimized according to the codon usage of *E. coli* for the efficient protein expression in *E. coli*. The N-termini of the two subunits of 2-oxoglutarate synthase and isocitrate dehydrogenase were linked to Strep-tag through polymerase chain reaction using the codon-optimized DNA fragments as templates. A forward primer set forth in SEQ ID NO: 13 and a reverse primer set forth in SEQ ID NO: 14 were used to construct the expression plasmid for the α-subunit of 2-oxoglutarate synthase, and a forward primer set forth in SEQ ID NO: 15 and a reverse primer set forth in SEQ ID NO: 16 were used to construct the expression plasmid for the β-subunit of 2-oxoglutarate synthase. Also, a forward primer set forth in SEQ ID NO: 17 and a reverse primer set forth in SEQ ID NO: 18 were used to construct the expression plasmid for isocitrate dehydrogenase. The forward primers of SEQ ID NOS: 13, 15 and 17 were designed to modify the start codon of proteins and insert the BsaI site as well. The reverse primers of SEQ ID NOS: 14, 16 and 18 were also designed to insert the BsaI site. All DNA fragments from polymerase chain reactions were ligated to protein expression vector pIBA7plus (IBA) containing a Strep-tag. As results, the N-termini of the two subunits of 2-oxoglutarate synthase and that of isocitrate dehydrogenase were linked to Strep-tag.

Example 3: Purification of Enzymes Including Carbon Dioxide Fixation Enzymes

Each of the α-subunit and β-subunit of succinyl-CoA synthetase set forth in SEQ ID NOS: 19 and 20, isocitrate lyase set forth in SEQ ID NO: 21, α-subunit and β-subunit of the 2-oxoglutarate synthase set forth in SEQ ID NOS: 22 and 23, and the isocitrate dehydrogenase set forth in SEQ ID NO: 24 were expressed in *E. coli* BL21 (DE3) and purified. *E. coli* BL21 (DE3) was transformed with each of the six expression plasmids constructed in Example 2. The recombinant *E. coli* strains were cultured in Luria-Bertani (LB) media whose usage is widely known. The expression and purification of the α-subunit and β-subunit of succinyl-CoA synthetase and isocitrate lyase were performed under aerobic condition. The recombinant *E. coli* strains were inoculated into a 1 L flask containing 500 mL LB medium and cultured on a shaker (250 revolutions per minute) at 30° C. under aerobic condition. Isopropyl β-D-thiogalactopyranoside (IPTG) was added at 0.4 mM when culture turbidity (absorbance at 600 nm, $A_{600}$) reached approximately 0.4. Then, cell culture continued for the induction of enzyme expression under the same growth condition until $A_{600}$ reached approximately 2.0. Cells were harvested by centrifugation at approximately 7,000 g at 4° C. for 10 minutes, followed by suspension in approximately 10 mL of 50 mM sodium dihydrogen phosphate ($NaH_2PO_4$) buffer (pH 7.9) at 4° C., which contains 10 mM imidazole, 250 mM sodium chloride (NaCl) and a protease inhibitor. Cells were sonicated four times, 5 minutes each with 50% due cycle on ice (total 20 minutes). The disrupted cells were centrifuged at approximately 10,000 g at 4° C. for 30 minutes to remove the unbroken cells and large cell debris. Finally, affinity purification using histidine-tag was performed to purify succinyl-CoA synthetase α- and β-subunits and isocitrate lyase according to the method recommended by manufacturer (Qiagen)

Conversely, recombinant *E. coli* strains expressing 2-oxoglutarate synthase α- and β-subunits and isocitrate dehydrogenase were cultured under aerobic condition, but the expression and purification of enzymes were performed under anaerobic condition. Recombinant *E. coli* BL21 (DE3) strains were inoculated into 300 mL flask containing 30 mL LB medium, and cultured on shaker (250 rpm) at 30° C. under aerobic condition. When the culture turbidity ($A_{600}$) reached approximately 1.0, cells were transferred to 4 L culture vessel, and the vessel was fully filled with LB medium. Then, culture vessel was bubbled with nitrogen gas for 5 minutes and plugged with butyl rubber stopper to avoid exposure to air. Then, cells were cultured at 30° C., and anhydrotetracycline was added at 0.2 µg/mL to induce the enzyme expression when culture turbidity ($A_{600}$) reached approximately 0.2. Culture continued under the same growth condition until $A_{600}$ reached approximately 1.0. All purification procedures of proteins were carried out in anaerobic chamber (Model 10, COY Lab) filled with a gas mixture of 5% hydrogen, 5% carbon dioxide, and 90% nitrogen, unless stated otherwise. Cells were harvested by centrifugation at 7,000 g at 4° C. for 10 minutes, followed by suspension in 20 mL of 100 mM Tris buffer (pH 8.0) at 4° C., which contains 150 mM sodium chloride and protease inhibitor. Cells were sonicated four times, 5 minutes each with 50% due cycle on ice (total 20 minutes) under anaerobic condition. The disrupted cells were centrifuged at approximately 10,000 g at 4° C. for 30 minutes to remove the unbroken cells and large cell debris. Finally, affinity purification using Strep-tag was performed to purify 2-oxoglutarate synthase α- and β-subunits, and isocitrate dehydrogenase according to the method recommended by manufacturer (IBA). The purified proteins were separated by 12% SDS-polyacrylamide gel (12%) electrophoresis to confirm the molecular mass of each enzyme, using the standard marker proteins.

Figure 3:
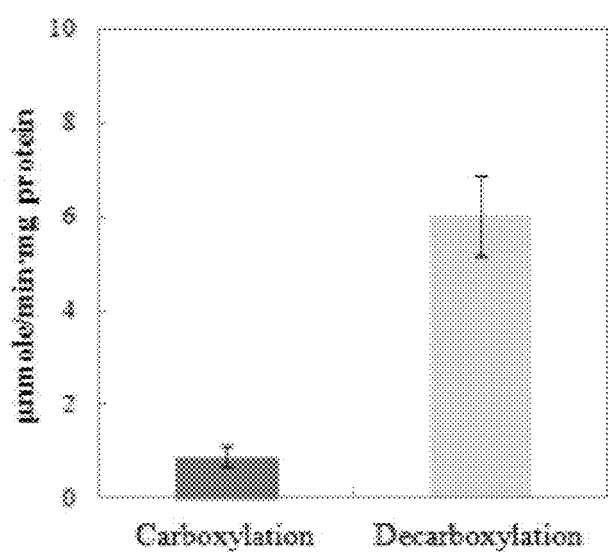
FIG. 3 shows the results of forward and reverse reaction activities of purified 2-oxoglutarate synthase. Carboxylation reaction is carried out by adding succinyl-CoA as substrate, and then a decrease in optical density at 340 nm according to the decrease in NADPH is examined to determine activity. On the other hand, decarboxylation reaction is carried out using 2-oxoglutarate as substrate and then an increase in optical density at 340 nm according to the formation of NADPH is examined to determine activity. Enzyme activity is shown by reaction rate in μmole/min·mg protein.

Example 4: Confirmation of Carbon Dioxide Fixation Activity of 2-Oxoglutarate Synthase 2-Oxoglutarate synthase is known to have different characteristic according to the source organism, and generally decarboxylation activity is preferred over carboxylation. However, since C. tepidum is a bacterium having ability to grow through carbon dioxide fixation by reductive citric acid cycle, it was predicted that the 2-oxoglutarate synthase of C. tepidum, which was purified as described in Example 3, easily showed carboxylation activity. To examine the carbon dioxide fixation in vitro, reaction mixture of 2-oxoglutarate synthase was prepared as follows: 100 µg ferredoxin, 0.05 U ferredoxin:NADP$^+$ reductase, 1 mM dithiothreitol, 1 mM magnesium chloride (MgCl$_2$), and 20 mM sodium hydrogen carbonate (NaHCO$_3$) were dissolved in 50 mM HEPES (4-(2-hydroxyethyl)piperazine-ethanesulfonic acid) buffer (pH 7.0). The ferredoxin and ferredoxin:NADP$^+$ reductase were derived from spinach. Carboxylation reaction of 2-oxoglutarate synthase was performed at 30° C. by adding 0.25 mM succinyl-CoA as a substrate and 0.25 mM NADPH as an electron donor to the reaction mixture. On the other hand, decarboxylation reaction of 2-oxoglutarate synthase was performed at 30° C. by adding 0.25 mM 2-oxoglutarate as a substrate and 0.25 mM NADP$^+$ as an electron acceptor to the reaction mixture. FIG. 3 shows the results of bidirectional activities of the purified 2-oxoglutarate synthase. It was revealed that 2-oxoglutarate synthase carried out carboxylation reaction using succinyl-CoA as a substrate, and showed the reaction rate of approximately 0.9 µmole/min·mg protein. 2-Oxoglutarate synthase also mediated decarboxylation reaction in the presence of 2-oxoglutarate, and showed a reaction rate of approximately 6.0 µmole/min·mg protein. Therefore, C. tepidum-derived 2-oxoglutarate synthase has relatively higher decarboxylation activity compared with carboxylation. However, carboxylation activity of 2-oxoglutarate synthase can be maintained dominantly over decarboxylation as long as succinyl-CoA is kept at higher level as compared with that of 2-oxoglutarate during reaction. In this example, ferredoxin was used to transfer electron to the 2-oxoglutarate synthase from NADPH by ferredoxin:NADP$^+$ reductase. The type of electron donor may also be easily selected from NADPH, NADH or pyruvate, and applied according to the types of the ferredoxin and ferredoxin:NADP$^+$ reductase by those skilled in the related art.

Figure 4:
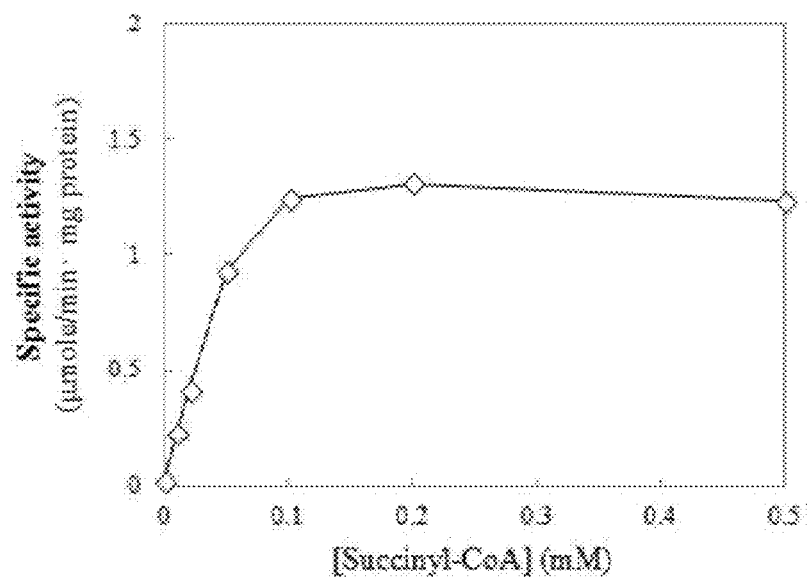
FIG. 4 shows the results of carboxylation reaction of 2-oxoglutarate synthase. Upper panel shows the specific activity of 2-oxoglutarate synthase at varying levels of succinyl-CoA. Lower panel shows the specific activity of 2-oxoglutarate synthase at varying levels of sodium hydrogen carbonate ($NaHCO_3$). In respective conditions, the enzyme reaction rate is expressed in μmole/min·mg protein.
Figure 4:
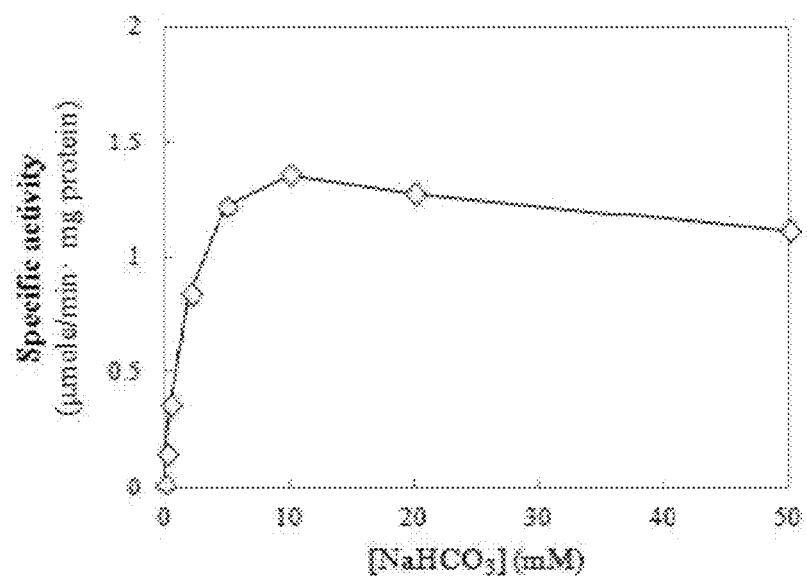

Example 5: Conditions for 2-Oxoglutarate Synthase-Mediated Carbon Dioxide Fixation 2-Oxoglutarate level was measured using various methods capable of selectively detecting 2-oxoglutarate (measuring a final product having optical density or fluorescence at certain wavelengths using enzymatic reaction, in which 2-oxoglutarate was consumed in proportion to the formation of the final product). The optimum method may be determined according to the purpose of research and development by those skilled in the related art. In this work, 2-oxoglutarate measurement kit (Sigma-Aldrich) was used to quantitatively measure the 2-oxoglutarate produced in this example. Reaction mixture was prepared as follows: 100 µg ferredoxin, 0.05 U ferredoxin:NADP$^+$ reductase, 1 mM dithiothreitol, 1 mM magnesium chloride, and 0.25 mM NADPH in 50 mM HEPES buffer (pH 7.0). 2-Oxoglutarate synthesis was determined by measuring the emission at 587 nm with respect to excitation at 535 nm using a spectrofluorometer. Standard curve was prepared, using 2-oxoglutarate measurement kit with the varying levels of 2-oxoglutarate. The level of 2-oxoglutarate after carboxylation reaction was determined from the standard curve. The level of the produced 2-oxoglutarate thus determined was expressed as a value with time, and the 2-oxoglutarate production rate was expressed in µmole of 2-oxoglutarate produced per minute per unit protein. An upper panel of FIG. 4 shows the results of carboxylation reaction of 2-oxoglutarate synthase by adding succinyl-CoA at varying levels to the reaction mixture. In this reaction, the concentration of sodium hydrogen carbonate was fixed at 20 mM. Based on the reaction results, carboxylation rate of 2-oxoglutarate synthase was saturated at maximum level when succinyl-CoA as the substrate was added at approximately 0.1 mM or more. A lower panel of FIG. 4 shows the results of carboxylation reaction of 2-oxoglutarate synthase in the presence of sodium hydrogen carbonate, which is another substrate of 2-oxoglutarate synthase, at varying levels. In this reaction, the concentration of succinyl-CoA was fixed at 0.25 mM. From the reaction results, the minimum concentration of sodium hydrogen carbonate for the maximum carboxylation rate of 2-oxoglutarate synthase was approximately 5 mM. In addition to the sodium hydrogen carbonate, it is possible to use various compounds forming carbonate in aqueous solution, or use carbon dioxide itself after it is dissolved in solution. The optimum carbon dioxide source and the use thereof can be determined according to the purpose of research and development by those skilled in the art.

Figure 5:
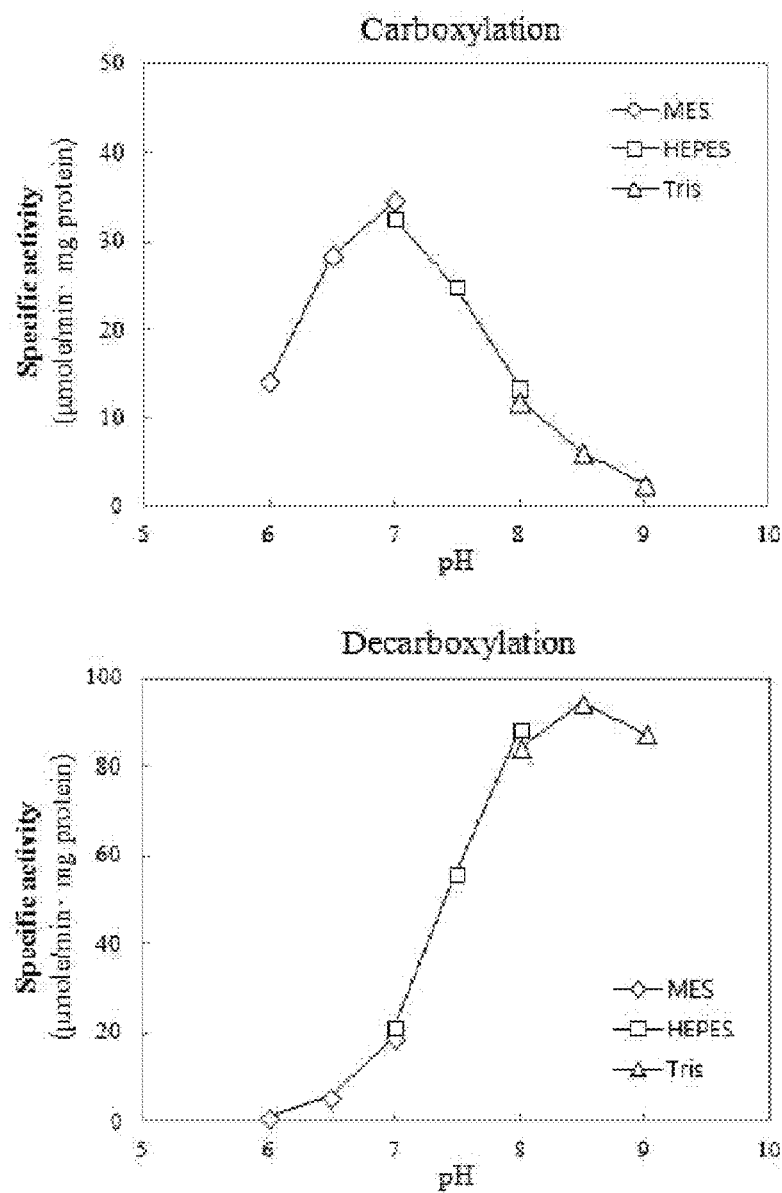
FIG. 5 shows carboxylation and decarboxylation activities of isocitrate dehydrogenase at varying pH. MES buffer is used to prepare a pH range of 6 to 7, HEPES buffer to prepare a pH range of 7 to 8, and Tris buffer to prepare a pH range of 8 to 9. Upper panel shows the carboxylation reaction rate of isocitrate dehydrogenase in the presence of 2-oxoglutarate at respective pH values. Lower panel shows the decarboxylation reaction rate of isocitrate dehydrogenase in the presence of isocitrate at respective pH values. In respective conditions, the enzyme reaction rate is expressed in μmole/min·mg protein.

Example 6: Confirmation of Carbon Dioxide Fixation Activity of Isocitrate Dehydrogenase Isocitrate dehydrogenase is known to have the preference for either decarboxylation or carboxylation activity according to pH (Lebedeva et al., 2002. *Microbiology* 71: 657-662). Therefore, Varying pH Conditions were Prepared to Determine decarboxylation and carboxylation activities of isocitrate dehydrogenase. 2-(N-morpholino)ethanesulfonic acid (MES) buffer was used to prepare a pH range of 6 to 7; HEPES buffer was used to prepare a pH range of 7 to 8; 2-amino-2-(hydroxymethyl)-1,3-propanediol (Tris) buffer was used to prepare a pH range of 8 to 9. The carboxylation activity of isocitrate dehydrogenase was examined in reaction mixture, which contains 8 mM 2-oxoglutarate as a substrate, 0.2 mM NADPH as an electron donor, 40 mM magnesium chloride (MgCl$_2$), and 20 mM sodium hydrogen carbonate (NaHCO$_3$) in 100 mM buffer. The reaction was performed at 30° C. Conversely, the decarboxylation activity of isocitrate dehydrogenase was examined in reaction mixture, which contains 0.4 mM isocitrate as a substrate, 0.2 mM NADP⁺ as an electron accepter, 40 mM magnesium chloride ($MgCl_2$), and 20 mM sodium hydrogen carbonate ($NaHCO_3$) in 100 mM buffer. The reaction was also performed at 30° C. Isocitrate, which is the carboxylation product of isocitrate dehydrogenase can be measured, using various methods capable of selectively detecting the compound (measuring a final product having optical density or fluorescence at certain wavelengths using enzymatic reaction, in which isocitrate was consumed in proportion to the formation of the final product). The optimum method can be determined according to the purpose of research and development by those skilled in the related art. An isocitrate measurement kit (Sigma-Aldrich) was used as a method of quantitatively measuring isocitrate formed in this example. On the other hand, 2-oxoglutarate, a decarboxylation product of isocitrate dehydrogenase was determined, using the method exemplified in Example 4. FIG. 5 shows enzymatic activities of the isocitrate dehydrogenase at varying pHs. Upper panel shows the carboxylation activity of isocitrate dehydrogenase under varying pH conditions. The isocitrate dehydrogenase had the optimum carboxylation activity at neutral pH 7.0. Lower panel shows the decarboxylation activity of isocitrate dehydrogenase under varying pH conditions. The isocitrate dehydrogenase had the optimum decarboxylation activity at weakly basic pH 8.5. Therefore, the isocitrate dehydrogenase of *C. tepidum* has relatively higher carboxylation activity as compared with the decarboxylation activity at neutral pH, and this property can be directly used for the carbon dioxide fixation using isocitrate dehydrogenase in vitro.

Example 7: Conditions for Isocitrate Dehydrogenase-Mediated Carbon Dioxide Fixation Kinetic characteristics of decarboxylation and carboxylation activities of isocitrate dehydrogenase were determined. FIG. 6 illustrates the kinetic results of decarboxylation and carboxylation activities of isocitrate dehydrogenase, which were determined at optimum pH of 8.5 and 7.0, respectively. The decarboxylation rate of isocitrate dehydrogenase, which uses isocitrate as a substrate and NADP⁺ as an electron accepter, was approximately 95 μmole/min·mg protein. The carboxylation rate of isocitrate dehydrogenase, which uses 2-oxoglutarate and sodium hydrogen carbonate as substrates and NADPH as an electron donor, was approximately 33 μmole/min·mg protein. The isocitrate dehydrogenase showed similar affinities for NADPH and NADP⁺, but the enzyme exhibited relatively higher affinity for isocitrate as compared to for 2-oxoglutarate. Because the affinity of isocitrate dehydrogenase of *C. tepidum* for sodium hydrogen carbonate was three times lower than those of the conventional isocitrate dehydrogenase isozymes, whose $K_m$ values for sodium hydrogen carbonate were known, the isocitrate dehydrogenase of *C. tepidum* seemed to be an enzyme having a relatively high tendency toward carboxylation. The enzyme had a higher decarboxylation rate based on $K_{cat}$ value. Accordingly, the 2-oxoglutarate level has to be maintained at higher level as compared with that of isocitrate in reaction mixture for carboxylation. In addition, the enzyme reaction will be carboxylation-favored under pH 7.0 condition. In addition to the sodium hydrogen carbonate, it is possible to use various compounds forming carbonate in aqueous solution, or use carbon dioxide itself after it is dissolved in solution. The optimum carbon dioxide source and the use thereof can be determined according to the purpose of research and development by those skilled in the art.

Example 8: Production of Glyoxylate Using Novel Carbon Dioxide Fixation Cycle

Figure 7:
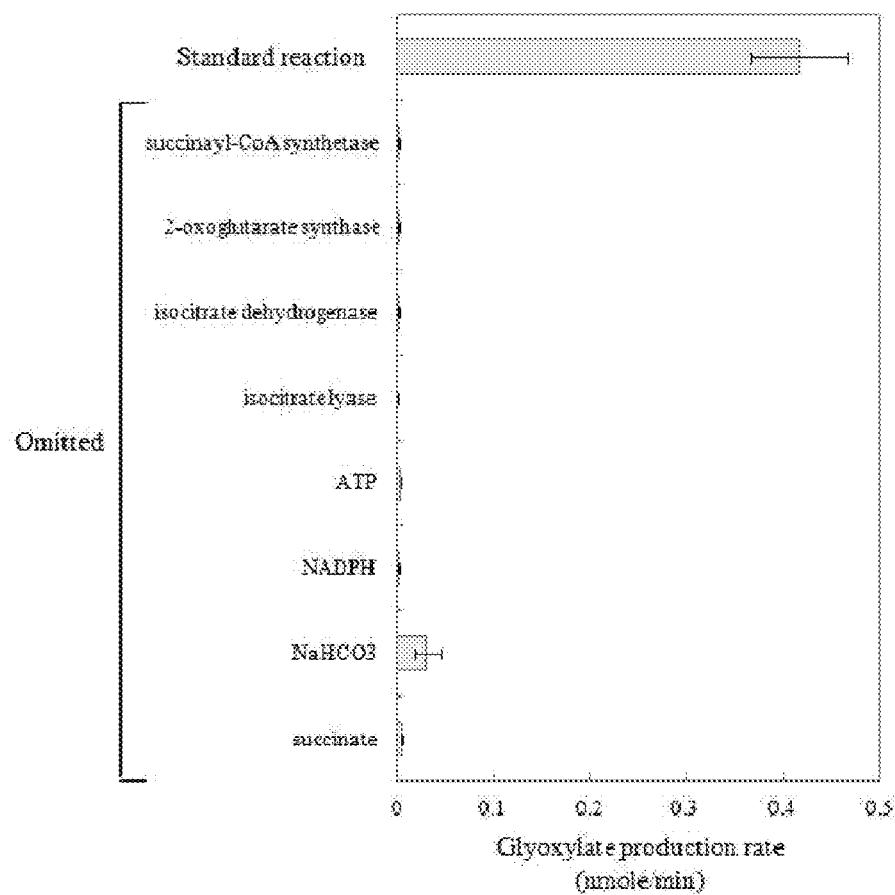
FIG. 7 shows the glyoxylate production using the reaction mixture, which includes the purified enzymes of succinyl-CoA synthetase, 2-oxoglutarate synthase, isocitrate dehydrogenase and isocitrate lyase. For standard reaction, reaction mixture contains enzymes (each at 10 μM), 0.5 mM NADPH, 1 mM adenosine triphosphate (ATP), 1 mM coenzyme A (CoA), 20 mM magnesium chloride (MgCl$_2$), 12.5 mM glutathione (GSH), 20 mM sodium hydrogen carbonate (NaHCO$_3$), and 5 mM succinate as initial substrate in 100 mM HEPES buffer (pH 7.0). To examine the effect of each component on reaction, each of succinyl-CoA synthetase, 2-oxoglutarate synthase, isocitrate dehydrogenase, isocitrate lyase, ATP, NADPH, sodium hydrogen carbonate, and succinate was omitted from the standard reaction mixture. In respective conditions, glyoxylate production rate is expressed in nmole/min.

In this example, glyoxylate was produced using the reaction mixture, which included all four enzymes constituting the novel carbon dioxide fixation cycle. Glyoxylate was measured according to the method known in the related art (McFadden. 1969. *Methods Enzymol.* 13: 163-170). Change in optical density of reaction solution at 520 nm was measured to determine glyoxylate by comparison to the standard curve, which had been prepared using the known levels of glyoxylate. FIG. 7 shows the glyoxylate production rate using the standard reaction mixture containing succinyl-CoA synthetase, 2-oxoglutarate synthase, isocitrate dehydrogenase and isocitrate lyase, which were isolated using the method exemplified in Example 3. Standard reaction mixture contains all four enzymes at 10 μM each, 0.5 mM NADPH, 1 mM ATP, 1 mM coenzyme A, 20 mM magnesium chloride, 12.5 mM glutathione, 20 mM sodium hydrogen carbonate, and 5 mM succinate as a starting material in 100 mM HEPES buffer (pH 7.0). To examine the effect of each component on glyoxylate production, reactions are performed in the reaction mixture devoid of one component, which could be either succinyl-CoA synthetase, 2-oxoglutarate synthase, isocitrate dehydrogenase, isocitrate lyase, ATP, NADPH, sodium hydrogen carbonate, or succinate. Glyoxylate was readily produced in standard reaction mixture. However, glyoxylate was hardly produced in the reaction mixture devoid of one component: when one of four enzymes was excluded from reaction, glyoxylate production was barely detected; when ATP or NADPH was excluded from reaction, the same was true. Conversely, even if sodium hydrogen carbonate was excluded from reaction, glyoxylate was still produced at 8% of the level from the standard reaction mixture. We assume that glyoxylate was synthesized, using carbon dioxide dissolved in buffer. Therefore, it could be seen that the carbon dioxide fixation cycle can work even at atmospheric carbon dioxide concentration to produce glyoxylate. In this example, succinate was used as a starting material of the carbon dioxide fixation cycle. Because glyoxylate was produced from the cycle, it was confirmed that four enzymes work together to form the cyclic reactions. Either succinyl-CoA, 2-oxoglutarate or isocitrate, which constitute the carbon dioxide fixation cycle, is applicable as a starting material of the carbon fixation cycle, and the optimum starting material and the use thereof can be determined according to the purpose of research and development by those skilled in the art.

Although the exemplary embodiments of the present invention have been described in detail, the present invention can be modified and implemented in various forms, and therefore, only specific embodiments are described in detail. However, the present invention is not limited to specific disclosures, and it should be understood that the present invention includes all modifications, equivalents and alternatives included in the technical idea and scope of the present invention.

What is claimed is:

1. An in vitro carbon dioxide ($CO_2$) fixation cycle, consisting of an α-subunit and a β-subunit of a succinyl CoA synthetase having SEQ ID NOs: 19 and 20, isocitrate lyase having SEQ ID NO: 21, α-subunit and β-subunit of a 2-oxoglutarate synthase having SEQ ID NOs: 22 and 23, and isocitrate dehydrogenase having SEQ ID NO: 24,
wherein:
said α-subunit and β-subunit of said succinyl-CoA synthetase converts succinate into succinyl-CoA, said α-subunit and β-subunit of said 2-oxoglutarate synthase converts succinyl-CoA into 2-oxoglutarate, an isocitrate dehydrogenase converts 2-oxoglutarate into isocitrate, and said isocitrate lyase converts isocitrate into succinate and glyoxylate;
a concentration of each of said succinate and said succinyl-CoA is maintained at ratio of 2:1 to 100:1;
a concentration of each of said succinyl-CoA and said 2-oxoglutarate is maintained at ratio of 100:1 to 10,000:1;
a concentration of each of sand 2-oxoglutarate and said isocitrate is maintained at ratio of 2:1 to 100:1;
a concentration of each of said isocitrate and said glyoxylate is maintained at ratio of 1:10 to 1:1,000; and
a fixation of carbon dioxide is carried out by carboxylation activity of one or more enzymes selected from the group consisting of said 2-oxoglutarate synthase and said isocitrate dehydrogenase.

2. The carbon dioxide fixation cycle of claim 1, wherein 2-oxoglutarate synthase is isolated from one or more strains selected from the group consisting of green sulfur bacteria, and chemolithotroph.

3. The carbon dioxide fixation cycle of claim 1, wherein isocitrate dehydrogenase is isolated from one or more strains selected from the group consisting of green sulfur bacteria, green non-sulfur bacteria, purple sulfur bacteria, purple non-sulfur bacteria, cyanobacteria, and chemolithotroph.

4. The carbon dioxide fixation cycle of claim 1, wherein the carboxylation activity of 2-oxoglutarate synthase is promoted by the reduced ferredoxin.

5. The carbon dioxide fixation cycle of claim 1, further comprising ferredoxin reductase that reduces ferredoxin to promote the carboxylation activity of 2-oxoglutarate synthase.

6. The carbon dioxide fixation cycle of claim 5, wherein the ferredoxin reductase is selected from the group consisting of ferredoxin:nicotinamide adenine dinucleotide phosphate reductase (ferredoxin:$NADP^+$ reductase), ferredoxin:nicotinamide adenine dinucleotide reductase (ferredoxin:$NAD^+$ reductase), and ferredoxin:pyruvate reductase.

7. The carbon dioxide fixation cycle of claim 1, further comprising adenosine triphosphate (ATP), one or more electron donors selected from the group consisting of carbonate ions ($CO_3^{2-}$) and carbon dioxide ($CO_2$), one or more electron donors selected from the group consisting of reduced nicotinamide adenine dinucleotide phosphate (NADPH), reduced nicotinamide adenine dinucleotide (NADH), and pyruvate to promote the carboxylation activity of 2-oxoglutarate synthase.

8. A method for fixing carbon dioxide using the $CO_2$ fixation cycle of claim 1, comprising:
supplying one or more carbon dioxide donors selected from the group consisting of carbonate ions ($CO_3^{-2}$) and carbon dioxide ($CO_2$) to the carbon fixation cycle of claim 1, which consists of succinyl-CoA synthetase, a 2-oxoglutarate synthase, isocitrate dehydrogenase, and isocitrate lyase.

9. The method of claim 8, wherein a carbohydrate product from carbon dioxide fixation is glyoxylate.

10. The method of claim 8, wherein one adenosine triphosphate (ATP) molecule is used as biochemical energy to fix one carbon dioxide molecule in the fixation method.

11. The method of claim 8, wherein two reduced nicotinamide adenine dinucleotide phosphate (NADPH) molecules are used as biochemical energy to fix two carbon dioxide molecules in the fixation method.

12. The method of claim 8, further comprising:
adding one or more carbohydrates selected from succinate, succinyl-CoA, oxoglutarate, and isocitrate as a starting material of the carbon dioxide fixation cycle.

13. The method of claim 12, wherein the carbohydrate serving as a starting material of the carbon dioxide fixation cycle is continuously regenerated and re-used without being consumed.

* * * * *

SEQUENCE LISTING

<160> NUMBER OF SEQ ID NOS: 24

<210> SEQ ID NO 1
<211> LENGTH: 870
<212> TYPE: DNA
<213> ORGANISM: Escherichia coli

<400> SEQUENCE: 1

```
atgtccattt taatcgataa aaacaccaag gttatctgcc agggctttac cggtagccag      60
gggactttcc actcagaaca ggccattgca tacggcacta aaatggttgg cggcgtaacc     120
ccaggtaaag gcggcaccac ccacctcggc ctgccggtgt tcaacaccgt gcgtgaagcc     180
gttgctgcca ctggcgctac cgcttctgtt atctacgtac cagcaccgtt ctgcaaagac     240
tccattctgg aagccatcga cgcaggcatc aaactgatta tcaccatcac tgaaggcatc     300
ccgacgctgg atatgctgac cgtgaaagtg aagctggatg aagcaggcgt tcgtatgatc     360
ggcccgaact gcccaggcgt tatcactccg ggtgaatgca aaatcggtat ccagcctggt     420
cacattcaca aaccgggtaa agtgggtatc gtttcccgtt ccggtacact gacctatgaa     480
gcggttaaac agaccacgga ttacggtttc ggtcagtcga cctgtgtcgg tatcggcggt     540
gacccgatcc cgggctctaa ctttatcgac attctcgaaa tgttcgaaaa agatccgcag     600
accgaagcga tcgtgatgat cggtgagatc ggcggtagcg ctgaagaaga agcagctgcg     660
tacatcaaag agcacgttac caagccagtt gtgggttaca tcgctggtgt gactgcgccg     720
aaaggcaaac gtatgggcca cgcgggtgcc atcattgccg gtgggaaagg gactgcggat     780
gagaaattcg ctgctctgga agccgcaggc gtgaaaaccg ttcgcagcct ggcggatatc     840
ggtgaagcac tgaaaactgt tctgaaataa                                      870
```

<210> SEQ ID NO 2
<211> LENGTH: 1167
<212> TYPE: DNA
<213> ORGANISM: Escherichia coli

<400> SEQUENCE: 2

```
atgaacttac atgaatatca ggcaaaacaa cttttttgccc gctatggctt accagcaccg      60
gtgggttatg cctgtactac tccgcgcgaa gcagaagaag ccgcttcaaa aatcggtgcc     120
ggtccgtggg tagtgaaatg tcaggttcac gctggtggcc gcggtaaagc gggcggtgtg     180
aaagttgtaa acagcaaaga agacatccgt gcttttgcag aaaactggct gggcaagcgt     240
ctggtaacgt atcaaacaga tgccaatggc caaccggtta ccagattct ggttgaagca     300
gcgaccgata tcgctaaaga gctgtatctc ggtgccgttg ttgaccgtag ttcccgtcgt     360
gtggtcttta tggcctccac cgaaggcggc gtggaaatcg aaaaagtggc ggaagaaact     420
ccgcacctga tccataaagt tgcgcttgat ccgctgactg gcccgatgcc gtatcaggga     480
cgcgagctgg cgttcaaact gggtctggaa ggtaaactgg ttcagcagtt caccaaaatc     540
ttcatgggcc tggcgaccat tttcctggag cgcgacctgg cgttgatcga aatcaacccg     600
ctggtcatca ccaaacaggg cgatctgatt tgcctcgacg caaactggg cgctgacggc     660
aacgcactgt tccgccagcc tgatctgcgc gaaatgcgtg accagtcgca ggaagatccg     720
cgtgaagcac aggctgcaca gtgggaactg aactacgttg cgctgacgg taacatcggt     780
tgtatggtta acggcgcagg tctggcgatg ggtacgatgg acatcgttaa actgcacggc     840
ggcgaaccgg ctaacttcct tgacgttggc ggcggcgcaa ccaaagaacg tgtaaccgaa     900
gcgttcaaaa tcatcctctc tgacgacaaa gtgaagccg ttctggttaa catcttcggc     960
```

```
ggtatcgttc gttgcgacct gatcgctgac ggtatcatcg gcgcggtagc agaagtgggt    1020
gttaacgtac cggtcgtggt acgtctggaa ggtaacaacg ccgaactcgg cgcgaagaaa    1080
ctggctgaca gcggcctgaa tattattgca gcaaaaggtc tgacggatgc agctcagcag    1140
gttgttgccg cagtggaggg gaaataa                                        1167
```

<210> SEQ ID NO 3
<211> LENGTH: 1305
<212> TYPE: DNA
<213> ORGANISM: Escherichia coli

<400> SEQUENCE: 3

```
atgaaaaccc gtacacaaca aattgaagaa ttacagaaag agtggactca accgcgttgg     60
gaaggcatta ctcgcccata cagtgcggaa gatgtggtga aattacgcgg ttcagtcaat    120
cctgaatgca cgctggcgca actgggcgca gcgaaaatgt ggcgtctgct gcacggtgag    180
tcgaaaaaag gctacatcaa cagcctcggc gcactgactg gcggtcaggc gctgcaacag    240
gcgaaagcgg gtattgaagc agtctatctg tcgggatggc aggtagcggc ggacgctaac    300
ctggcggcca gcatgtatcc ggatcagtcg ctctatccgg caaactcggt gccagctgtg    360
gtggagcgga tcaacaacac cttccgtcgt gccgatcaga tccaatggtc cgcgggcatt    420
gagccgggcg atccgcgcta tgtcgattac ttcctgccga tcgttgccga tgcggaagcc    480
ggttttggcg gtgtcctgaa tgcctttgaa ctgatgaaag cgatgattga agccggtgca    540
gcggcagttc acttcgaaga tcagctggcg tcagtgaaga atgcggtca catgggcggc    600 aaagttttag tgccaactca ggaagctatt cagaaactgg tcgcggcgcg tctggcagct    660
gacgtgacgg cgttccaac cctgctggtt gcccgtaccg atgctgatgc ggcggatctg    720
atcacctccg attgcgaccc gtatgacagc gaatttatta ccggcgagcg taccagtgaa    780
ggcttcttcc gtactcatgc gggcattgag caagcgatca gccgtggcct ggcgtatgcg    840
ccatatgctg acctggtctg tgtgaaacc tccacgccgg atctggaact ggcgcgtcgc    900
tttgcacaag ctatccacgc gaaatatccg ggcaaactgc tggcttataa ctgctcgccg    960
tcgttcaact ggcagaaaaa cctcgacgac aaaactattg ccagcttcca gcagcagctg   1020
tcggatatgg gctacaagtt ccagttcatc accctggcag gtatccacag catgtggttc   1080
aacatgtttg acctggcaaa cgcctatgcc cagggcgagg gtatgaagca ctacgttgag   1140
aaagtgcagc agccggaatt tgccgccgcg aaagatggct ataccttcgt atctcaccag   1200
caggaagtgg gtacaggtta cttcgataaa gtgacgacta ttattcaggg cggcacgtct   1260
tcagtcaccg cgctgaccgg ctccactgaa gaatcgcagt tctaa                   1305
```

<210> SEQ ID NO 4
<211> LENGTH: 1884
<212> TYPE: DNA
<213> ORGANISM: Artificial Sequence
<220> FEATURE:
<223> OTHER INFORMATION: a codon optimized gene coding for
      2-oxoglutarate synthase subunit alpha of Chlorobium tepidum

<400> SEQUENCE: 4

```
atgagtgata ccgtaatctt aaacaacaat gatatggtaa tctcaaaaac caacgtgtca     60 gtgcttttg caggtgactc cggtgacggc atgcagctta caggcaccca gttgccaac    120 acggtggccc tttacggttc ggacttgaat acttttccga actttccttc tgagatcaga    180
cctcctgccg gtaccgtggc tggagtttca ggctttcaat tgcagtttgg cacaaccggt    240
```

```
gtctatacac cgggcgcgaa atttgatgta atgatcgcta tgaatgctgc cgcgctgaaa    300
gcaaatctga agaacctgca tcatggtggt atcatcattg ctgataccga tgggttttgac   360 gcaaagaact taaacttagc tggttacggt gaaaccaaca atccgctcga agatggcacg    420
ctgactgatt ataccgtatt taaaattccg gttataagcc tcacgcgaca agcgttggcc    480
gatacaggcc tgtcaaccaa gatcatcgac cgttgcaaaa atatgtttgt gctcggcgtg    540
ctctattggt tatatagctt accattagag accacgattg aggcattgca gtcaaaattt    600
aagaataaac aggacattgc cgaagccaat ataaaagcag tcaaggcagg gtataatttc    660
ggcgatgaaa ccgagatgtt cagtcaacat ggtcgttttt gtgttccgcc ggcccagaaa    720
aaaaagggtg tttatcgccg cgtgactgga aatgaagcta gtgctattgg tcttgccgca    780
gccgcacaaa aggctggact ggaactcttc cttggatcct atccgatcac cccggcttcc    840
gaaattttgc agacccttgc ggggttgaaa aaatggggcg ttaaaacgtt tcaggctgaa    900
gacgaaatag ccggtatcct gaccagtatc ggcgccgcgt atggaggtgc tcttgccgcc    960
actaacacca gcggtcccgg gctggcgtta aaaaccgaag ggatgggttt ggcggttatc   1020
ttagagcttc ctctggtgat catcaatgtt atgcgtggag gcccgtcaac aggactgccg   1080
actaaacctg agcagtctga tctgctcatg gctatgtacg gacgtcacgg cgaagcgccc   1140
atgccggtca tagcggccat gtctccggtt gactgcttct atgccgccta tgaagcggcg   1200
aagatagccg tcgagtacat gacacctgta ctttgtctca ccgatggcta tctcgcactc   1260
agctctgaac cgatgctagt gccatctcct gatgaactgg cttctatcac tcccatgttt   1320
agtccagaac ggaaagccga tgatccgccg tatctgccgt acaagcgcga cgagcgctgc   1380
gtcaggccgt ggggcatccc cggtactccc ggtctggaac accgcatagg aggtctagaa   1440
aaacagaatg aaacgggcca tgtttcgcat gatcctgaga accatgcact catgaccaga   1500
ttgcgggctg aaaaagtagc aaaagtggca gatattattc ctgatcttac gatagataat   1560
ggcccggaaa aaggggatct actcgtctta gggtggggtt cgacatatgg cgccattaag   1620
aaagcagtcg aacaagctcg cgaaggagga cttgacgttg cccacgcgca cttacgctat   1680
ataaacccgt ttccgaaaaa tctcggcgcg atgctcggaa acttcaaaaa agtgttaatt   1740
cccgaaaaca attgtggtca actgcttagc ctcattcgtg ataaattcct cattgagcct   1800
gtagggttta gcaaagttca ggggctgccg ttcaatgaga tggaaatcga agaaaaaatc   1860
actgatatct taaaggagct ctaa                                          1884
```

<210> SEQ ID NO 5
<211> LENGTH: 1029
<212> TYPE: DNA
<213> ORGANISM: Artificial Sequence
<220> FEATURE:
<223> OTHER INFORMATION: a codon optimized gene coding for
2-oxoglutarate synthase subunit beta of Chlorobium tepidum

<400> SEQUENCE: 5

```
atgaccgata cacataccctg tcttactgcc aaagatttca cgagtaacca agaaccgaaa    60
tggtgccccg ctgtggtga tttcatggtt ctccagcaac tcaaaaatgc gatggctgaa    120
ctgtgcctga aaacggaaga ggtagtcgtg gtatcgggta ttggatgcag ctcaaggctg    180
ccatattata tcaataccta tggcgtgcac ggcattcatg ggcgcgcaat ggcgatggcg    240
tcaggtctga agttgcacg tcccgacctc agcgtttggg ttgcacagg cgatggcgat    300 gctctctcta ttggcggtaa ccattacata catactgtcc gacggaacct cgatatcaat    360
```

```
gtggtgctgt ttaataacga gatttacggt ctaactaaag gtcagtattc cccaacatca    420
aaagtgggtt tgagaaccgt aacatctcct accggggtgg tggattatcc gatcaacacg    480
atagccctga cgcttggcgc aggtggtaca tttgttgccc gtgtcatgga tcgcgatgga    540
aagctgatga aggagatttt taaacgtgcc cacaatcata aagggacctc aatagtcgag    600
atatatcaga attgtccgat ttttaatgat ggagctttta gagccttctc tgataaggag    660
cggaaagatg acactacact ttatctggaa cagggccagc cgttagtttt tggggcgaac    720
gggagtaagg gaatctacct ggacggtttt aaaccaacgg tgattgacct cgaaaagagc    780
ggcgtttcca aagatgactt atggattcac gacgaaaatg acctcatcaa ggcaaatatc    840
ttatcgcgct tcttcgacga tccgaatagt accgaagagt ttctccctcg tccttttggt    900 atttttatg tagaggaccg cttcacctac gaacaggctt taagtgcaca aatcgataaa    960
gcgcaggaaa aaggagaagg gaccttggaa gaactgcttg ctggcaacag cacgtggacc    1020
attaattaa                                                           1029

<210> SEQ ID NO 6
<211> LENGTH: 2226
<212> TYPE: DNA
<213> ORGANISM: Artificial Sequence
<220> FEATURE:
<223> OTHER INFORMATION: a codon optimized gene coding for isocitrate
      dehydrogenase of Chlorobium tepidum

<400> SEQUENCE: 6
atggcaagca aatcaaccat tatttacact aagaccgacg aggctccggc tttggcgaca     60
tattcgctgt tacctatcat ccaggccttc acccggggca caggcgttga tgtcgagatg    120
agggatatct cccttgccgg cagaatcatt gccaacttcc cggagaatct tacagaggcc    180
cagagaattc ccgactattt aagtcagcta ggtgaattag tgctggcgcc tgaggccaac    240
atcatcaagc ttccaaatat tagcgctagt attccccaac tgaaagccgc catcaaggag    300
cttcaggaac atggttacaa cgtgccagac tatcctgaag ccccgtcaaa tgacgaagaa    360
aaagcgattc aagccagata tgcaaaggtg cttggtagcg ccgtgaaccc ggtgcttcga    420
gaaggtaact ccgaccgtcg tgcaccgctc tcagtgaaag cttacgccaa gaagcatcca    480
caccggatgg ctgcatggtc tgtcaattct aaagcgcacg tttcctatat gactgatggt    540 gattttacg gcagcgagca gtctgtaaca gtgcctgccg ccaccacggt tcgtatcgaa    600
tatgttaacg gtgccaacga agtgactgtg ctgaaagaga aaaccgcact gctcgcgggt    660
gaagtgattg acacgtcagt tatgaatgtg cgcaagctca gagagttcta tgccgagcag    720
attgaggatg ccaaatcgca gggcgtgctt ttttctctgc acctgaaagc taccatgatg    780
aagatttcag atccggtcat gtttggccat gccgtgtctg tctttttataa agatgtgttt    840 gacaaacatg gggcattgtt agccgagttg ggggtgaacg tcaataacgg ccttggtgat    900
ctctatgcca aaatccaaac cctacctgaa gataaacgtg ccgagatcga ggctgacatc    960
atggcggttt acaaaacccg tcccgagctg gcgatggtcg attctgataa gggcatcacc    1020
aatctgcacg tgccaaacga tataatcatc gatgcttcta tgcctgtcgt tgtgcgcgat    1080
ggtggcaaaa tgtggggccc cgacggtcag cttcatgact gcaaagctgt gattccggat    1140
cgatgctacg ctacgatgta cggcgaaatc gtggacgact gtcgaaaaaa cggcgccttt    1200
gatccttcca ctatcggatc agtaccgaac gtgggactta tggcgcagaa ggctgaagag    1260
tacggttcgc atgacaaaac ctttatcgcg cctggggacg gcgtgatccg cgtggtcgat    1320
```

```
gccgatggta gtgtgctcat gtctcaaaaa gtcgaaactg gcgacatatt taggatgtgt   1380
cagacaaaag atgctccgat tcgcgactgg gtgaaactgg ctgtccgccg cgccaaagct   1440
acgggtgctc cagcagtctt ttggttggac agtaaccgcg ctcatgatgc gcaaatcatc   1500
gccaaagtga atgagtatct caaagacctc gacactgacg gcgtcgagat caagattatg   1560
cctccggtcg aagccatgcg gtttaccttg ggtcgtttcc gtgccggaca agacaccata   1620
tcagtgactg gaaatgtgct tcgtgattac ctgaccgacc tgttcccgat aatcgaactt   1680
ggaacaagct ccaagatgtt atcgattgtt ccgttattaa acggtggtgg tctgtttgaa   1740
accggtgcag gcggttctgc tcccaaacat gtgcaacagt tccagaaaga gggctatcta   1800
cgctgggatt cgctcggcga gttcttggct ctgaccgcat ctctggaaca cctcgcccag   1860
acctttggca accctaaagc acaggtatta gccgacacgc tcgaccaggc aatcggcaag   1920
tttctcgaaa atcagaaatc gccagcgcgt aaagtcggcc aaatagataa tcgcggcagc   1980
catttctatc tcgcgctcta ttgggccgaa gcgttggcca gtcaggatgc ggatgccgaa   2040
atgaaggctc gctttgccgg tgttgcacaa gcgctcgcag agaaagagga actcatcaac   2100
gccgagctga ttgccgcgca aggaagccca gtcgatatag gtggctatta ccagccggat   2160
gacgagaaaa ccactcgcgc catgcgtccc agcgggaccc tcaatgcgat aattaatgcc   2220
atgtaa                                                               2226

<210> SEQ ID NO 7
<211> LENGTH: 33
<212> TYPE: DNA
<213> ORGANISM: Artificial Sequence
<220> FEATURE:
<223> OTHER INFORMATION: SucD forward primer

<400> SEQUENCE: 7
aaaaaaggat cctccatttt aatcgataaa aac                                  33

<210> SEQ ID NO 8
<211> LENGTH: 33
<212> TYPE: DNA
<213> ORGANISM: Artificial Sequence
<220> FEATURE:
<223> OTHER INFORMATION: SucD reverse primer

<400> SEQUENCE: 8
aaaaaaaagc ttttttcagaa cagttttcag tgc                                 33

<210> SEQ ID NO 9
<211> LENGTH: 32
<212> TYPE: DNA
<213> ORGANISM: Artificial Sequence
<220> FEATURE:
<223> OTHER INFORMATION: SucC forward primer

<400> SEQUENCE: 9
aaaaaagaat tcaacttaca tgaatatcag gc                                   32

<210> SEQ ID NO 10
<211> LENGTH: 30
<212> TYPE: DNA
<213> ORGANISM: Artificial Sequence
<220> FEATURE:
<223> OTHER INFORMATION: SucC reverse primer

<400> SEQUENCE: 10
```

-continued aaaaaaggat cctttcccct ccactgcggc                                      30

<210> SEQ ID NO 11
<211> LENGTH: 34
<212> TYPE: DNA
<213> ORGANISM: Artificial Sequence
<220> FEATURE:
<223> OTHER INFORMATION: AceA forward primer

<400> SEQUENCE: 11
aaaaaaggat ccaaaacccg tacacaacaa attg                                 34

<210> SEQ ID NO 12
<211> LENGTH: 32
<212> TYPE: DNA
<213> ORGANISM: Artificial Sequence
<220> FEATURE:
<223> OTHER INFORMATION: AceA reverse primer

<400> SEQUENCE: 12
aaaaaaaagc ttgaactgcg attcttcagt gg                                   32

<210> SEQ ID NO 13
<211> LENGTH: 41
<212> TYPE: DNA
<213> ORGANISM: Artificial Sequence
<220> FEATURE:
<223> OTHER INFORMATION: OgsA forward primer

<400> SEQUENCE: 13
aaaaaaggtc tcagcgcatg agtgataccg taatcttaaa c                         41

<210> SEQ ID NO 14
<211> LENGTH: 39
<212> TYPE: DNA
<213> ORGANISM: Artificial Sequence
<220> FEATURE:
<223> OTHER INFORMATION: OgsA reverse primer

<400> SEQUENCE: 14
aaaaaaggtc tcttatcatt agagctcctt taagatatc                            39

<210> SEQ ID NO 15
<211> LENGTH: 37
<212> TYPE: DNA
<213> ORGANISM: Artificial Sequence
<220> FEATURE:
<223> OTHER INFORMATION: OgsB forward primer

<400> SEQUENCE: 15
aaaaaaggtc tcagcgcatg accgatacac atacctg                              37

<210> SEQ ID NO 16
<211> LENGTH: 38
<212> TYPE: DNA
<213> ORGANISM: Artificial Sequence
<220> FEATURE:
<223> OTHER INFORMATION: OgsB reverse primer

<400> SEQUENCE: 16
aaaaaaggtc tcttatcatt aattaatggt ccacgtgc                             38

<210> SEQ ID NO 17
<211> LENGTH: 39
<212> TYPE: DNA
<213> ORGANISM: Artificial Sequence -continued

```
<220> FEATURE:
<223> OTHER INFORMATION: Icd forward primer

<400> SEQUENCE: 17
aaaaaaggtc tcagcgcatg gcaagcaaat caaccatta                              39

<210> SEQ ID NO 18
<211> LENGTH: 39
<212> TYPE: DNA
<213> ORGANISM: Artificial Sequence
<220> FEATURE:
<223> OTHER INFORMATION: Icd reverse primer

<400> SEQUENCE: 18
aaaaaaggtc tcttatcatt acatggcatt aattatcgc                              39

<210> SEQ ID NO 19
<211> LENGTH: 289
<212> TYPE: PRT
<213> ORGANISM: Escherichia coli

<400> SEQUENCE: 19
```

| Met | Ser | Ile | Leu | Ile | Asp | Lys | Asn | Thr | Lys | Val | Ile | Cys | Gln | Gly | Phe |
|---|---|---|---|---|---|---|---|---|---|---|---|---|---|---|---|
| 1 | | | | 5 | | | | | 10 | | | | | 15 | |

Thr Gly Ser Gln Gly Thr Phe His Ser Glu Gln Ala Ile Ala Tyr Gly
            20                  25                  30

Thr Lys Met Val Gly Gly Val Thr Pro Gly Lys Gly Thr Thr His
        35                  40                  45

Leu Gly Leu Pro Val Phe Asn Thr Val Arg Glu Ala Val Ala Ala Thr
 50                  55                  60

Gly Ala Thr Ala Ser Val Ile Tyr Val Pro Ala Pro Phe Cys Lys Asp
 65                  70                  75                  80

Ser Ile Leu Glu Ala Ile Asp Ala Gly Ile Lys Leu Ile Ile Thr Ile
                85                  90                  95

Thr Glu Gly Ile Pro Thr Leu Asp Met Leu Thr Val Lys Val Lys Leu
            100                 105                 110

Asp Glu Ala Gly Val Arg Met Ile Gly Pro Asn Cys Pro Gly Val Ile
            115                 120                 125

Thr Pro Gly Glu Cys Lys Ile Gly Ile Gln Pro Gly His Ile His Lys
 130                 135                 140

Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
        195                 200                 205

Glu Ile Gly Gly Ser Ala Glu Glu Ala Ala Tyr Ile Lys Glu
    210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu

Lys

<210> SEQ ID NO 20
<211> LENGTH: 388
<212> TYPE: PRT
<213> ORGANISM: Escherichia coli

<400> SEQUENCE: 20

```
Met Asn Leu His Glu Tyr Gln Ala Lys Gln Leu Phe Ala Arg Tyr Gly
  1               5                  10                  15
Leu Pro Ala Pro Val Gly Tyr Ala Cys Thr Thr Pro Arg Glu Ala Glu
                 20                  25                  30
Glu Ala Ala Ser Lys Ile Gly Ala Gly Pro Trp Val Val Lys Cys Gln
             35                  40                  45
Val His Ala Gly Gly Arg Gly Lys Ala Gly Gly Val Lys Val Val Asn
     50                  55                  60
Ser Lys Glu Asp Ile Arg Ala Phe Ala Glu Asn Trp Leu Gly Lys Arg
 65                  70                  75                  80
Leu Val Thr Tyr Gln Thr Asp Ala Asn Gly Gln Pro Val Asn Gln Ile
                 85                  90                  95
Leu Val Glu Ala Ala Thr Asp Ile Ala Lys Glu Leu Tyr Leu Gly Ala
            100                 105                 110
Val Val Asp Arg Ser Ser Arg Arg Val Val Phe Met Ala Ser Thr Glu
        115                 120                 125
Gly Gly Val Glu Ile Glu Lys Val Ala Glu Glu Thr Pro His Leu Ile
    130                 135                 140
His Lys Val Ala Leu Asp Pro Leu Thr Gly Pro Met Pro Tyr Gln Gly
145                 150                 155                 160
Arg Glu Leu Ala Phe Lys Leu Gly Leu Glu Gly Lys Leu Val Gln Gln
                165                 170                 175
Phe Thr Lys Ile Phe Met Gly Leu Ala Thr Ile Phe Leu Glu Arg Asp
            180                 185                 190
Leu Ala Leu Ile Glu Ile Asn Pro Leu Val Ile Thr Lys Gln Gly Asp
        195                 200                 205
Leu Ile Cys Leu Asp Gly Lys Leu Gly Ala Asp Gly Asn Ala Leu Phe
    210                 215                 220
Arg Gln Pro Asp Leu Arg Glu Met Arg Asp Gln Ser Gln Glu Asp Pro
225                 230                 235                 240
Arg Glu Ala Gln Ala Gln Trp Glu Leu Asn Tyr Val Ala Leu Asp
                245                 250                 255
Gly Asn Ile Gly Cys Met Val Asn Gly Ala Gly Leu Ala Met Gly Thr
            260                 265                 270
Met Asp Ile Val Lys Leu His Gly Gly Glu Pro Ala Asn Phe Leu Asp
        275                 280                 285
Val Gly Gly Gly Ala Thr Lys Glu Arg Val Thr Glu Ala Phe Lys Ile
    290                 295                 300
Ile Leu Ser Asp Asp Lys Val Lys Ala Val Leu Val Asn Ile Phe Gly
305                 310                 315                 320
Gly Ile Val Arg Cys Asp Leu Ile Ala Asp Gly Ile Ile Gly Ala Val
                325                 330                 335
Ala Glu Val Gly Val Asn Val Pro Val Val Val Arg Leu Glu Gly Asn
            340                 345                 350
Asn Ala Glu Leu Gly Ala Lys Lys Leu Ala Asp Ser Gly Leu Asn Ile
```

```
                    355                 360                 365
Ile Ala Ala Lys Gly Leu Thr Asp Ala Ala Gln Gln Val Val Ala Ala
                370                 375                 380

Val Glu Gly Lys
385

<210> SEQ ID NO 21
<211> LENGTH: 434
<212> TYPE: PRT
<213> ORGANISM: Escherichia coli

<400> SEQUENCE: 21

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335
```

```
Gln Gln Gln Leu Ser Asp Met Gly Tyr Lys Phe Gln Phe Ile Thr Leu
                340                 345                 350

Ala Gly Ile His Ser Met Trp Phe Asn Met Phe Asp Leu Ala Asn Ala
            355                 360                 365

Tyr Ala Gln Gly Glu Gly Met Lys His Tyr Val Glu Lys Val Gln Gln
        370                 375                 380

Pro Glu Phe Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
                420                 425                 430

Gln Phe

<210> SEQ ID NO 22
<211> LENGTH: 627
<212> TYPE: PRT
<213> ORGANISM: Chlorobium tepidum

<400> SEQUENCE: 22

Met Ser Asp Thr Val Ile Leu Asn Asn Asn Asp Met Val Ile Ser Lys
1               5                   10                  15

Thr Asn Val Ser Val Leu Phe Ala Gly Asp Ser Gly Asp Gly Met Gln
                20                  25                  30

Leu Thr Gly Thr Gln Phe Ala Asn Thr Val Ala Val Tyr Gly Ser Asp
            35                  40                  45

Leu Asn Thr Phe Pro Asn Phe Pro Ser Glu Ile Arg Pro Pro Ala Gly
        50                  55                  60

Thr Val Ala Gly Val Ser Gly Phe Gln Leu Gln Phe Gly Thr Thr Gly
65              70                  75                  80

Val Tyr Thr Pro Gly Ala Lys Phe Asp Val Met Ile Ala Met Asn Ala
                85                  90                  95

Ala Ala Leu Lys Ala Asn Leu Lys Asn Leu His His Gly Gly Ile Ile
                100                 105                 110

Ile Ala Asp Thr Asp Gly Phe Asp Ala Lys Asn Leu Asn Leu Ala Gly
            115                 120                 125

Tyr Gly Glu Thr Asn Asn Pro Leu Glu Asp Gly Thr Leu Thr Asp Tyr
        130                 135                 140

Thr Val Phe Lys Ile Pro Val Ile Ser Leu Thr Arg Gln Ala Leu Ala
145                 150                 155                 160

Asp Thr Gly Leu Ser Thr Lys Ile Ile Asp Arg Cys Lys Asn Met Phe
                165                 170                 175

Val Leu Gly Val Leu Tyr Trp Leu Tyr Ser Leu Pro Leu Glu Thr Thr
                180                 185                 190

Ile Glu Ala Leu Gln Ser Lys Phe Lys Asn Lys Gln Asp Ile Ala Glu
            195                 200                 205

Ala Asn Ile Lys Ala Val Lys Ala Gly Tyr Asn Phe Gly Asp Glu Thr
        210                 215                 220

Glu Met Phe Ser Gln His Gly Arg Phe Cys Val Pro Pro Ala Gln Lys
225                 230                 235                 240

Lys Lys Gly Val Tyr Arg Arg Val Thr Gly Asn Glu Ala Ser Ala Ile
                245                 250                 255

Gly Leu Ala Ala Ala Gln Lys Ala Gly Leu Glu Leu Phe Leu Gly
            260                 265                 270
```

```
Ser Tyr Pro Ile Thr Pro Ala Ser Glu Ile Leu Gln Thr Leu Ala Gly
            275                 280                 285

Leu Lys Lys Trp Gly Val Lys Thr Phe Gln Ala Glu Asp Glu Ile Ala
        290                 295                 300

Gly Ile Leu Thr Ser Ile Gly Ala Ala Tyr Gly Gly Ala Leu Ala Ala
305                 310                 315                 320

Thr Asn Thr Ser Gly Pro Gly Leu Ala Leu Lys Thr Glu Gly Met Gly
                325                 330                 335

Leu Ala Val Ile Leu Glu Leu Pro Val Ile Ile Asn Val Met Arg
            340                 345                 350

Gly Gly Pro Ser Thr Gly Leu Pro Thr Lys Pro Glu Gln Ser Asp Leu
        355                 360                 365

Leu Met Ala Met Tyr Gly Arg His Gly Glu Ala Pro Met Pro Val Ile
370                 375                 380

Ala Ala Met Ser Pro Val Asp Cys Phe Tyr Ala Ala Tyr Glu Ala Ala
385                 390                 395                 400

Lys Ile Ala Val Glu Tyr Met Thr Pro Val Leu Cys Leu Thr Asp Gly
                405                 410                 415

Tyr Leu Ala Leu Ser Ser Glu Pro Met Leu Val Pro Ser Pro Asp Glu
            420                 425                 430

Leu Ala Ser Ile Thr Pro Met Phe Ser Pro Glu Arg Lys Ala Asp Asp
        435                 440                 445

Pro Pro Tyr Leu Pro Tyr Lys Arg Asp Glu Arg Cys Val Arg Pro Trp
    450                 455                 460

Gly Ile Pro Gly Thr Pro Gly Leu Glu His Arg Ile Gly Gly Leu Glu
465                 470                 475                 480

Lys Gln Asn Glu Thr Gly His Val Ser His Asp Pro Glu Asn His Ala
                485                 490                 495

Leu Met Thr Arg Leu Arg Ala Glu Lys Val Ala Lys Val Ala Asp Ile
            500                 505                 510

Ile Pro Asp Leu Thr Ile Asp Asn Gly Pro Lys Gly Asp Leu Leu
        515                 520                 525

Val Leu Gly Trp Gly Ser Thr Tyr Gly Ala Ile Lys Lys Ala Val Glu
530                 535                 540

Gln Ala Arg Glu Gly Gly Leu Asp Val Ala His Ala His Leu Arg Tyr
545                 550                 555                 560

Ile Asn Pro Phe Pro Lys Asn Leu Gly Ala Met Leu Gly Asn Phe Lys
                565                 570                 575

Lys Val Leu Ile Pro Glu Asn Asn Cys Gly Gln Leu Leu Ser Leu Ile
            580                 585                 590

Arg Asp Lys Phe Leu Ile Glu Pro Val Gly Phe Ser Lys Val Gln Gly
        595                 600                 605

Leu Pro Phe Asn Glu Met Glu Ile Glu Glu Lys Ile Thr Asp Ile Leu
    610                 615                 620

Lys Glu Leu
625

<210> SEQ ID NO 23
<211> LENGTH: 342
<212> TYPE: PRT
<213> ORGANISM: Chlorobium tepidum

<400> SEQUENCE: 23

Met Thr Asp Thr His Thr Cys Leu Thr Ala Lys Asp Phe Thr Ser Asn
1               5                   10                  15
```

Gln Glu Pro Lys Trp Cys Pro Gly Cys Gly Asp Phe Met Val Leu Gln
                20                  25                  30

Gln Leu Lys Asn Ala Met Ala Glu Leu Cys Leu Lys Thr Glu Glu Val
            35                  40                  45

Val Val Val Ser Gly Ile Gly Cys Ser Ser Arg Leu Pro Tyr Tyr Ile
    50                  55                  60

Asn Thr Tyr Gly Val His Gly Ile His Gly Arg Ala Met Ala Met Ala
65                  70                  75                  80

Ser Gly Leu Lys Val Ala Arg Pro Asp Leu Ser Val Trp Val Gly Thr
                85                  90                  95

Gly Asp Gly Asp Ala Leu Ser Ile Gly Gly Asn His Tyr Ile His Thr
            100                 105                 110

Val Arg Arg Asn Leu Asp Ile Asn Val Val Leu Phe Asn Asn Glu Ile
    115                 120                 125

Tyr Gly Leu Thr Lys Gly Gln Tyr Ser Pro Thr Ser Lys Val Gly Leu
130                 135                 140

Arg Thr Val Thr Ser Pro Thr Gly Val Val Asp Tyr Pro Ile Asn Thr
145                 150                 155                 160

Ile Ala Leu Thr Leu Gly Ala Gly Gly Thr Phe Val Ala Arg Val Met
                165                 170                 175

Asp Arg Asp Gly Lys Leu Met Lys Glu Ile Phe Lys Arg Ala His Asn
            180                 185                 190

His Lys Gly Thr Ser Ile Val Glu Ile Tyr Gln Asn Cys Pro Ile Phe
    195                 200                 205

Asn Asp Gly Ala Phe Arg Ala Phe Ser Asp Lys Glu Arg Lys Asp Asp
210                 215                 220

Thr Thr Leu Tyr Leu Glu Gln Gly Gln Pro Leu Val Phe Gly Ala Asn
225                 230                 235                 240

Gly Ser Lys Gly Ile Tyr Leu Asp Gly Phe Lys Pro Thr Val Ile Asp
                245                 250                 255

Leu Glu Lys Ser Gly Val Ser Lys Asp Asp Leu Trp Ile His Asp Glu
            260                 265                 270

Asn Asp Leu Ile Lys Ala Asn Ile Leu Ser Arg Phe Phe Asp Asp Pro
    275                 280                 285

Asn Ser Thr Glu Glu Phe Leu Pro Arg Pro Phe Gly Ile Phe Tyr Val
290                 295                 300

Glu Asp Arg Phe Thr Tyr Glu Gln Ala Leu Ser Ala Gln Ile Asp Lys
305                 310                 315                 320

Ala Gln Glu Lys Gly Glu Gly Thr Leu Glu Glu Leu Leu Ala Gly Asn
                325                 330                 335

Ser Thr Trp Thr Ile Asn
            340

<210> SEQ ID NO 24
<211> LENGTH: 741
<212> TYPE: PRT
<213> ORGANISM: Chlorobium tepidum

<400> SEQUENCE: 24

Met Ala Ser Lys Ser Thr Ile Ile Tyr Thr Lys Thr Asp Glu Ala Pro
1               5                   10                  15

Ala Leu Ala Thr Tyr Ser Leu Leu Pro Ile Ile Gln Ala Phe Thr Arg
            20                  25                  30

Gly Thr Gly Val Asp Val Glu Met Arg Asp Ile Ser Leu Ala Gly Arg

```
              35                  40                  45
Ile Ile Ala Asn Phe Pro Glu Asn Leu Thr Glu Ala Gln Arg Ile Pro
 50                  55                  60

Asp Tyr Leu Ser Gln Leu Gly Glu Leu Val Leu Ala Pro Glu Ala Asn
 65                  70                  75                  80

Ile Ile Lys Leu Pro Asn Ile Ser Ala Ser Ile Pro Gln Leu Lys Ala
                 85                  90                  95

Ala Ile Lys Glu Leu Gln Glu His Gly Tyr Asn Val Pro Asp Tyr Pro
                100                 105                 110

Glu Ala Pro Ser Asn Asp Glu Lys Ala Ile Gln Ala Arg Tyr Ala
                115                 120                 125

Lys Val Leu Gly Ser Ala Val Asn Pro Val Leu Arg Glu Gly Asn Ser
    130                 135                 140

Asp Arg Arg Ala Pro Leu Ser Val Lys Ala Tyr Ala Lys Lys His Pro
145                 150                 155                 160

His Arg Met Ala Ala Trp Ser Val Asn Ser Lys Ala His Val Ser Tyr
                    165                 170                 175

Met Thr Asp Gly Asp Phe Tyr Gly Ser Glu Gln Ser Val Thr Val Pro
                180                 185                 190

Ala Ala Thr Thr Val Arg Ile Glu Tyr Val Asn Gly Ala Asn Glu Val
                195                 200                 205

Thr Val Leu Lys Glu Lys Thr Ala Leu Leu Ala Gly Glu Val Ile Asp
    210                 215                 220

Thr Ser Val Met Asn Val Arg Lys Leu Arg Glu Phe Tyr Ala Glu Gln
225                 230                 235                 240

Ile Glu Asp Ala Lys Ser Gln Gly Val Leu Phe Ser Leu His Leu Lys
                    245                 250                 255

Ala Thr Met Met Lys Ile Ser Asp Pro Val Met Phe Gly His Ala Val
                260                 265                 270

Ser Val Phe Tyr Lys Asp Val Phe Asp Lys His Gly Ala Leu Leu Ala
                275                 280                 285

Glu Leu Gly Val Asn Val Asn Asn Gly Leu Gly Asp Leu Tyr Ala Lys
    290                 295                 300

Ile Gln Thr Leu Pro Glu Asp Lys Arg Ala Glu Ile Glu Ala Asp Ile
305                 310                 315                 320

Met Ala Val Tyr Lys Thr Arg Pro Glu Leu Ala Met Val Asp Ser Asp
                    325                 330                 335

Lys Gly Ile Thr Asn Leu His Val Pro Asn Asp Ile Ile Asp Ala
                340                 345                 350

Ser Met Pro Val Val Arg Asp Gly Gly Lys Met Trp Gly Pro Asp
    355                 360                 365

Gly Gln Leu His Asp Cys Lys Ala Val Ile Pro Asp Arg Cys Tyr Ala
    370                 375                 380

Thr Met Tyr Gly Glu Ile Val Asp Asp Cys Arg Lys Asn Gly Ala Phe
385                 390                 395                 400

Asp Pro Ser Thr Ile Gly Ser Val Pro Asn Val Gly Leu Met Ala Gln
                405                 410                 415

Lys Ala Glu Glu Tyr Gly Ser His Asp Lys Thr Phe Ile Ala Pro Gly
                420                 425                 430

Asp Gly Val Ile Arg Val Val Asp Ala Asp Gly Ser Val Leu Met Ser
    435                 440                 445

Gln Lys Val Glu Thr Gly Asp Ile Phe Arg Met Cys Gln Thr Lys Asp
    450                 455                 460
```

```
Ala Pro Ile Arg Asp Trp Val Lys Leu Ala Val Arg Arg Ala Lys Ala
465                 470                 475                 480

Thr Gly Ala Pro Ala Val Phe Trp Leu Asp Ser Asn Arg Ala His Asp
            485                 490                 495

Ala Gln Ile Ile Ala Lys Val Asn Glu Tyr Leu Lys Asp Leu Asp Thr
            500                 505                 510

Asp Gly Val Glu Ile Lys Ile Met Pro Pro Val Glu Ala Met Arg Phe
            515                 520                 525

Thr Leu Gly Arg Phe Arg Ala Gly Gln Asp Thr Ile Ser Val Thr Gly
530                 535                 540

Asn Val Leu Arg Asp Tyr Leu Thr Asp Leu Phe Pro Ile Ile Glu Leu
545                 550                 555                 560

Gly Thr Ser Ser Lys Met Leu Ser Ile Val Pro Leu Leu Asn Gly Gly
                565                 570                 575

Gly Leu Phe Glu Thr Gly Ala Gly Gly Ser Ala Pro Lys His Val Gln
            580                 585                 590

Gln Phe Gln Lys Glu Gly Tyr Leu Arg Trp Asp Ser Leu Gly Glu Phe
        595                 600                 605

Leu Ala Leu Thr Ala Ser Leu Glu His Leu Ala Gln Thr Phe Gly Asn
    610                 615                 620

Pro Lys Ala Gln Val Leu Ala Asp Thr Leu Asp Gln Ala Ile Gly Lys
625                 630                 635                 640

Phe Leu Glu Asn Gln Lys Ser Pro Ala Arg Lys Val Gly Gln Ile Asp
                645                 650                 655

Asn Arg Gly Ser His Phe Tyr Leu Ala Leu Tyr Trp Ala Glu Ala Leu
            660                 665                 670

Ala Ser Gln Asp Ala Asp Ala Glu Met Lys Ala Arg Phe Ala Gly Val
        675                 680                 685

Ala Gln Ala Leu Ala Glu Lys Glu Glu Leu Ile Asn Ala Glu Leu Ile
    690                 695                 700

Ala Ala Gln Gly Ser Pro Val Asp Ile Gly Gly Tyr Tyr Gln Pro Asp
705                 710                 715                 720

Asp Glu Lys Thr Thr Arg Ala Met Arg Pro Ser Gly Thr Leu Asn Ala
                725                 730                 735

Ile Ile Asn Ala Met
            740
```